United States Patent
McMullen et al.

(10) Patent No.: US 12,357,473 B2
(45) Date of Patent: Jul. 15, 2025

(54) LAMINOPLASTY IMPLANT SYSTEMS AND METHODS

(71) Applicant: Gregory Thomas Gdowski, Rochester, NY (US)

(72) Inventors: Alex James McMullen, Rochester, NY (US); Megan Luzenski, Milford, MI (US); Aaron Joseph Craig, Saint Paul, MN (US); Gregory Thomas Gdowski, Rochester, NY (US); Martin Gira, Hilton, NY (US)

( * ) Notice: Subject to any disclaimer, the term of this patent is extended or adjusted under 35 U.S.C. 154(b) by 274 days.

(21) Appl. No.: 18/306,793

(22) Filed: Apr. 25, 2023

(65) Prior Publication Data

US 2023/0338165 A1 Oct. 26, 2023

Related U.S. Application Data

(60) Provisional application No. 63/363,522, filed on Apr. 25, 2022.

(51) Int. Cl.
| | |
|---|---|
| *A61B 17/70* | (2006.01) |
| *A61B 17/17* | (2006.01) |
| *A61F 2/46* | (2006.01) |
| *A61F 2/30* | (2006.01) |
| *A61F 2/44* | (2006.01) |

(52) U.S. Cl.
CPC ........ *A61F 2/4611* (2013.01); *A61B 17/1757* (2013.01); *A61F 2002/30327* (2013.01); *A61F 2002/3085* (2013.01); *A61F 2002/448* (2013.01); *A61F 2002/4615* (2013.01)

(58) Field of Classification Search
CPC .... A61B 17/70; A61B 17/7071; A61F 2/4611
USPC ......................................................... 606/246
See application file for complete search history.

(56) References Cited

U.S. PATENT DOCUMENTS

| | | | |
|---|---|---|---|
| 6,080,157 | A | 6/2000 | Cathro et al. |
| 6,572,617 | B1 | 6/2003 | Senegas |
| 6,635,087 | B2 | 10/2003 | Angelucci et al. |
| 6,712,852 | B1 | 3/2004 | Chung et al. |
| 8,133,280 | B2 | 3/2012 | Voellmicke et al. |
| 8,147,528 | B2 | 4/2012 | Mazzuca et al. |
| 8,172,875 | B2 | 5/2012 | Taylor |
| 8,246,682 | B2 | 8/2012 | Slivka et al. |
| 8,518,081 | B2 | 8/2013 | Patel et al. |
| 8,529,570 | B2 | 9/2013 | Mehdizade |

(Continued)

*Primary Examiner* — Eduardo C Robert
*Assistant Examiner* — Christina Negrellirodriguez
(74) *Attorney, Agent, or Firm* — Heslin Rothenberg Farley & Mesiti P.C.

(57) ABSTRACT

A laminoplasty implant system includes a spacer implant configured for insertion into an interlaminal space defined by a cut into a lamina of a vertebra. The spacer implant includes a first end and a second end, and a tunnel extending axially between the first end and the second end. The laminoplasty implant system also includes a single fastener implant configured for insertion through the tunnel when the spacer implant is inserted into the interlaminal space. The fastener implant includes a head and a fastener portion. The head is configured to abut against a portion of the spacer implant and to extend axially from the first end into the lamina of the vertebra. The fastener portion is configured to extend through the tunnel and to extend axially from the second end into a lateral mass of the vertebra.

20 Claims, 19 Drawing Sheets

(56) References Cited

U.S. PATENT DOCUMENTS

| | | |
|---|---|---|
| 9,138,264 B2 | 9/2015 | Bucci et al. |
| 9,155,569 B2 | 10/2015 | Konieczynski et al. |
| 9,211,152 B2 | 12/2015 | Zalenski et al. |
| 9,480,503 B2 | 11/2016 | Khanna |
| 9,750,552 B2 | 9/2017 | Stephan et al. |
| 9,795,420 B2 | 10/2017 | Voellmicke et al. |
| 9,968,380 B2 | 5/2018 | Robinson |
| 9,974,590 B2 | 5/2018 | Farin |
| 10,039,646 B2 | 8/2018 | Shepard et al. |
| 10,105,234 B2 | 10/2018 | Squires et al. |
| 10,226,284 B2 | 3/2019 | Suh et al. |
| 10,238,434 B2 | 3/2019 | Ricica et al. |
| 10,314,621 B2 | 6/2019 | Null et al. |
| 10,413,336 B2 | 9/2019 | Koch et al. |
| 10,568,665 B2 | 2/2020 | Millhouse et al. |
| 10,667,916 B2 | 6/2020 | Tacca et al. |
| 10,682,164 B2 | 6/2020 | Stevenson et al. |
| 10,695,107 B2 | 6/2020 | Squires et al. |
| 10,709,483 B2 | 7/2020 | Voellmicke et al. |
| 10,869,698 B2 | 12/2020 | Perryman et al. |
| 2010/0057127 A1* | 3/2010 | McGuire ............ A61B 17/8023 606/70 |
| 2010/0185239 A1* | 7/2010 | Patel ................. A61B 17/7071 606/264 |
| 2022/0061901 A1* | 3/2022 | Linder ............... A61B 17/8004 |

* cited by examiner

302: Inserting a spacer implant mimic disposed on a second leg of a handle of a drill guide into an interlaminal space cut into a lamina of a vertebra. The spacer implant mimic having substantially the same geometric shape as a spacer implant, wherein both the spacer implant mimic and spacer implant include a first end, a second end and a tunnel extending therebetween.

304: Positioning a first drill guide slider mate of the drill guide over a first leg of the handle such that a first drill guide hole disposed in the first drill guide slider mate has substantially the same center line as the tunnel of the spacer implant mimic.

306: Utilizing the first drill guide hole as a guide to drill a first pilot hole into the lateral mass of the vertebral body.

308: Positioning a second drill guide slider mate of the drill guide over the first leg of the handle such that a second drill guide hole disposed in the second drill guide slider mate has substantially the same center line as the tunnel of the spacer implant mimic.

310: Utilizing the second drill guide hole as a guide to drill a second pilot hole into the resected lamina of the vertebral body.

312: Inserting the spacer implant into the interlaminal space in place of the spacer implant mimic.

314: Implanting a fastener implant through the second pilot hole in the resected lamina, the tunnel of the spacer implant and the first pilot hole in the lateral mass of the vertebral body to secure the spacer implant and fastener implant in place within the interlaminal space.

316: Removing a spinous process from the vertebral body prior to drilling the first and second pilot holes.

FIG. 18

400 ↓ 402
Inserting one of a spacer implant or a spacer implant mimic disposed on a second leg of a handle of a drill guide, into an interlaminal space cut into a lamina of a vertebral body. The spacer implant mimic has substantially the same geometric shape as the spacer implant, wherein both the spacer implant mimic and spacer implant include a first end, a second end and a tunnel extending therebetween.

↓ 404
Positioning one or more drill guide slider mates of the drill guide over a first leg of the handle such that one or more drill guide holes disposed in the one or more drill guide slider mates has substantially the same center line as a tunnel of the respective one of the spacer implant or spacer implant mimic.

↓ 406
Utilizing the one or more drill guide holes as one or more guides to drill a first pilot hole into a lateral mass of the vertebral body and a second pilot hole into the cut lamina of the vertebral body.

↓ 408
Detaching the spacer implant from the drill guide, if the spacer implant is attached to the second leg of the drill guide.

↓ 410
Inserting the spacer implant into the interlaminal space in place of the spacer implant mimic, if the spacer implant mimic is attached to the second leg of the drill guide.

↓ 412
Implanting a fastener implant through the second pilot hole in the cut lamina, the tunnel of the spacer implant and the first pilot hole in the lateral mass of the vertebral body to secure the spacer implant and fastener implant in place within the interlaminal space.

LAMINOPLASTY IMPLANT SYSTEMS AND METHODS

TECHNICAL FIELD

The present disclosure relates to spinal implant systems and methods used during surgery. More specifically, the disclosure relates to laminoplasty implant systems and methods used during a laminoplasty procedure.

BACKGROUND OF THE INVENTION

The spinal canal (or vertebral foramen) of a vertebra may become narrowed (smaller in cross-sectional area) due to spinal stenosis caused by a variety of conditions or events, such as, for example trauma, age, diseases and/or ossification. When the spinal canal of a vertebrae is narrowed, pressure may be put on the spinal nerves or spinal cord passing through and cause severe pain/discomfort, numbness and weakness in extremities, and in more severe cases bladder and bowel dysfunction or paralysis.

Laminoplasty is a surgical procedure that enlarges the spinal canal to relieve such pressure put on the spinal nerves or spinal canal. Laminoplasty is performed on a section of bone of a vertebra called a lamina, which forms a roof like structure over the spinal canal. During an open-door laminoplasty, a hinge may be created on one side of the lamina while the other side is cut through to allow placement of a wedge, spacer, implant or implant system that will lift the laminar body, thereby increasing the cross-sectional area of the spinal canal and relieving the stenosis. Laminoplasty may be performed on, for example, cervical vertebrae in the neck, thoracic vertebrae in the middle back, and/or lumbar vertebrae in the lower back.

Problematically, previous laminoplasty spinal implant systems require multiple fasteners, such as bone screws, to secure and fix the implant to the vertebrae. Often a single laminoplasty implant system may require 3 to 6 or more screws, and many laminoplasty cases require multiple laminoplasty implants to correct multiple vertebral segments/levels. Each additional screw increases the chances of one or more screws slipping off of the screwdriver or, worse, being dropped into the vertebral foramen during surgery. Screws dropped in the vertebral foramen run the risk of puncturing the dura mater and retrieving the screw may lead to complications. Additionally, multiple screws require multiple drilling procedures into the bone, which increases the chances of damage to the bone and lengthens the procedure. Overall, the more screws required to fasten the laminoplasty implant, the more time consuming and cumbersome the laminoplasty procedure is for the surgeon which increases the risks for the patient.

Accordingly, there is a need for a laminoplasty implant system and method, which utilizes a minimum number of fasteners, such as screws. There is also a need for laminoplasty implant system and method, which may utilize a single fastener.

SUMMARY OF THE INVENTION

The present disclosure offers advantages and alternatives over the prior art by providing laminoplasty implant systems and methods which utilize a single fastener to secure and fix an implant to a vertebra.

A laminoplasty implant system in accordance with one or more aspects of the present disclosure includes a spacer implant configured for insertion into an interlaminal space defined by a cut into a lamina of a vertebrae. The spacer implant includes a first end and a second end, and a tunnel extending axially between the first end and the second end. The laminoplasty spacer implant also includes a single fastener implant configured for insertion through the tunnel when the spacer implant is inserted into the interlaminal space. The fastener implant includes a head and a fastener portion. The head is configured to abut against a portion of the spacer implant and to extend axially from the first end into the lamina of the vertebrae. The fastener portion is configured to extend through the tunnel and to extend axially from the second end into a lateral mass of the vertebrae.

A laminoplasty implant system in accordance with one or more aspects of the present disclosure includes a spacer implant configured for insertion into an interlaminal space defined by a cut into a lamina of a vertebrae. The spacer implant includes a first end and a second end, and a tunnel extending axially between the first and second ends. The tunnel includes a large diameter section having a first diameter and a small diameter section having a second diameter smaller than the first diameter. The large and small diameter sections define a hard-stop therebetween. The laminoplasty implant system also includes a single fastener implant configured for insertion through the tunnel when the spacer implant is inserted into the interlaminal space. The fastener implant includes a head and a fastener portion. The head is configured to abut against the hard-stop and to extend outwardly from the first end and into the lamina of the vertebrae. The fastener portion is configured to extend outwardly from the second end and into a lateral mass of the vertebrae.

A method of implanting a spacer implant into an interlaminal space of a vertebrae in accordance with one or more aspects of the present disclosure includes inserting one of a spacer implant or a spacer implant mimic, disposed on a second leg of a handle of a drill guide, into an interlaminal space defined by a cut into a lamina of a vertebrae. The spacer implant mimic has substantially the same geometric shape as the spacer implant. Both the spacer implant mimic and spacer implant include a first end, a second end and a tunnel extending therebetween. One or more drill guide slider mates of the drill guide are positioned over a first leg of the handle such that one or more drill guide holes disposed in the one or more drill guide slider mates have substantially the same center line as a tunnel of the respective one of the spacer implant or spacer implant mimic. The one or more drill guide holes are utilized as one or more guides to drill a first pilot hole into a lateral mass of the vertebrae, and a second pilot hole into the lamina of the vertebrae. The spacer implant is detached from the drill guide, if the spacer implant is attached to the second leg of the drill guide. The spacer implant is inserted into the interlaminal space in place of the spacer implant mimic, if the spacer implant mimic is attached to the second leg of the drill guide. A fastener implant is implanted through the second pilot hole in the lamina, the tunnel of the spacer implant and the first pilot hole in the lateral mass to secure the spacer implant and fastener implant in place within the interlaminal space.

Another method of implanting a spacer implant into an interlaminal space of a vertebrae in accordance with one or more aspects of the present disclosure includes inserting a spacer implant mimic disposed on a second leg of a handle of a drill guide into an interlaminal space defined by a cut into a lamina of a vertebrae. The spacer implant mimic has substantially the same geometric shape as a spacer implant. Both the spacer implant mimic and spacer implant include a first end, a second end and a tunnel extending therebetween. A first drill guide slider mate of the drill guide is positioned over a first leg of the handle such that a first drill guide hole disposed in the first drill guide slider mate has substantially the same center line as the tunnel of the spacer implant mimic. The first drill guide hole is utilized as a guide to drill a first pilot hole into the lateral mass of the vertebrae. A second drill guide slider mate of the drill guide is positioned over the first leg of the handle such that a second drill guide hole disposed in the second drill guide slider mate has substantially the same center line as the tunnel of the spacer implant mimic. The second drill guide hole is utilized as a guide to drill a second pilot hole into the lamina of the vertebrae. The spacer implant is inserted into the interlaminal space in place of the spacer implant mimic. A fastener implant is implanted through the second pilot hole in the lamina, the tunnel of the spacer implant and the first pilot hole in the lateral mass to secure the spacer implant and fastener implant in place within the interlaminal space.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

BRIEF DESCRIPTION OF THE DRAWINGS

The disclosure will be more fully understood from the following detailed description taken in conjunction with the accompanying drawings, in which:

FIG. 17 depicts a flow diagram of the method of implanting a spacer implant into an interlaminal space of a vertebral body as illustrated in FIGS. 10-15, according to aspects described herein; and FIG. 18 depicts a flow diagram of another method of implanting a spacer implant into an interlaminal space of a vertebral body according to aspects described herein.

DETAILED DESCRIPTION OF THE INVENTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "significantly", "substantially", "approximately", "about", "relatively," or other such similar terms that may be used throughout this disclosure, including the claims, are used to describe and account for small fluctuations, such as due to variations in processing from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Figure 1:
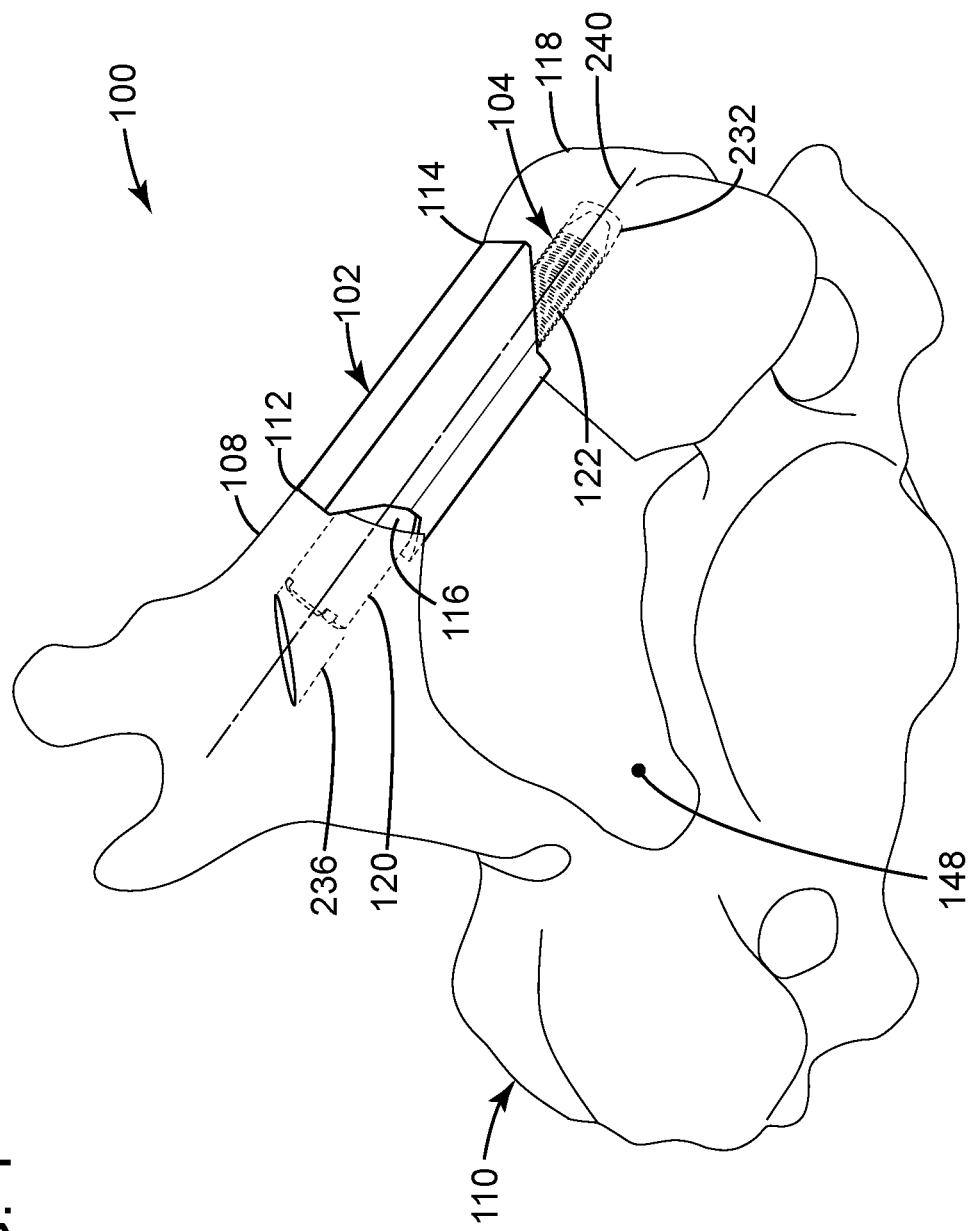
FIG. 1 depicts a perspective view of a laminoplasty implant system, according to aspects described herein.
Figure 2:
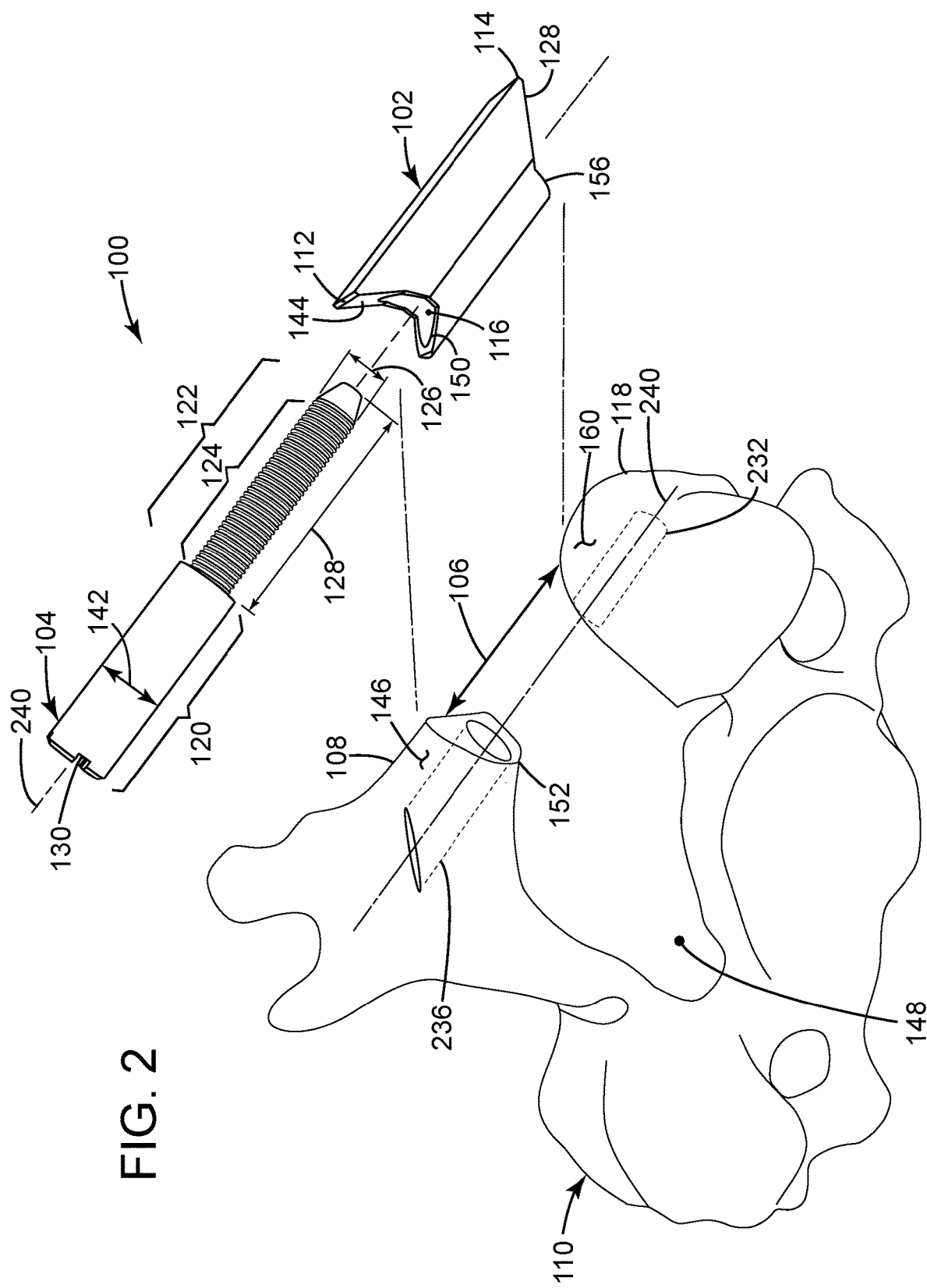
FIG. 2 depicts an exploded view of the laminoplasty implant system of FIG. 1, according to aspects described herein.

Referring to FIGS. 1 and 2, a perspective view (FIG. 1) and an exploded view (FIG. 2) of a laminoplasty implant system 100 is depicted, according to aspects described herein. The laminoplasty implant system 100 may include a spacer implant 102, a fastener implant 104 and, as will be discussed in greater detail herein, a drill guide 200 (see FIGS. 6 and 7). The spacer implant 102 and fastener implant 104 are what ultimately remain in an interlaminal space 106 of a vertebra or vertebral body 110 after a laminoplasty procedure. Advantageously, the spacer implant 102 is fixated to the vertebra 110 using a single fastener implant 104, rather than multiple screws or implants as used on previous laminoplasty implant systems.

The spacer implant 102 and fastener implant 104 may be made from medical grade, biocompatible materials. For example, the spacer implant 102 and fastener implant 104 may be made from, but not limited to, titanium alloy Ti6A14V per ASTM International (ASTM) standard F136.

The spacer implant 102, is configured for insertion into the interlaminal space 106, which is cut into the lamina 108 of the vertebra 110. The spacer implant 102 includes a first end 112 and a second end 114. The first end 112 may also be referred to as the laminal end 112, because the first end abuts the lamina 108 of the vertebra 110. The second end 114 may also be referred to as the lateral mass end 114, because the second end abuts the lateral mass 118 of the vertebra 110. The spacer implant 102 also includes a tunnel 116, which extends axially between the first end 112 and the second end 114.

As will be discussed in greater detail herein, the first end 112 of the spacer implant 102 may include a superficial laminal flange 144 extending over a superficial surface 146 of the lamina 108 and a deep laminal flange 150 extending over a deep surface 152 of the lamina 108. Additionally, the second end 114 of the spacer implant 102 may also include a lateral mass kick stand surface 156 abutting against the lateral mass 118 and a lateral mass flange 158 extending over a superficial surface 160 of the lateral mass 118. The superficial laminal flange 144 and the lateral mass flange 158 help to prevent the spacer implant 102 from inadvertently being pushed into the vertebral foramen (spinal canal) 148 of the vertebra 110. Whereas the deep laminal flange 150 provides a shelf for the deep surface of the lamina 152 to rest on, preventing the deep surface 152 from moving into the vertebral foramen 148.

The vertebra 110 illustrated in FIGS. 1 and 2 is a cervical vertebra. However, the laminoplasty implant system 102 may be used in other vertebrae as well. By way of example, the laminoplasty implant may be used in a thoracic vertebrae and/or a lumbar vertebrae.

The single fastener implant 104 is configured for insertion through the tunnel 116 when the spacer implant 102 is inserted into the interlaminal space 106. The fastener implant 104 includes a head (or head portion) 120 and a fastener portion 122. The head 120 is configured to abut against a portion of the spacer implant 102 to provide a hard stop 140 (see FIG. 3A) that prevents the fastener portion 122 from penetrating too far into the lateral mass 118. The head portion 120 also extends axially outward from the first end 112 into the lamina 108 of the vertebra 110 to help anchor and fix the lamina 108 in place.

The fastener portion 122 is configured to extend through the tunnel 116. The fastener portion 122 is also configured to extend axially outward from the second end 114 into the lateral mass 118 of the vertebra 110 to anchor and fix the lateral mass 118 in place.

The fastener portion 122 as illustrated in FIGS. 1 and 2, includes a threaded section 124 configured to be threaded into a first pilot hole 232 bored into the lateral mass 118 of the vertebra 110. The threaded portion 124 has a major thread diameter 126 that is designed to grip into the bone within the first pilot hold 232 of the vertebra 110. The threaded portion may be, for example, in conformance with ASTM F543—"Standard Specification and Test Methods for Metallic Medical Bone Screws".

Figure 3A:
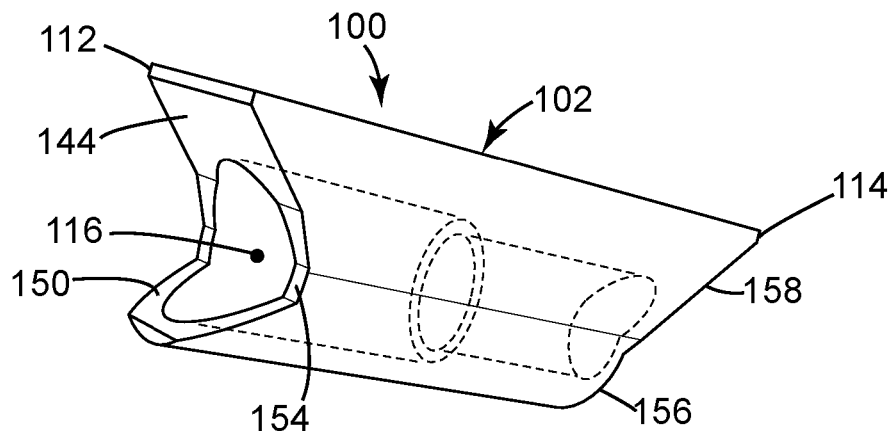
FIG. 3A depicts a perspective view of an embodiment of a spacer implant of a laminoplasty implant system, wherein the geometry of the tunnel of the spacer implant is shown in hidden dotted lines therein, according to aspects described herein.
Figure 3B:
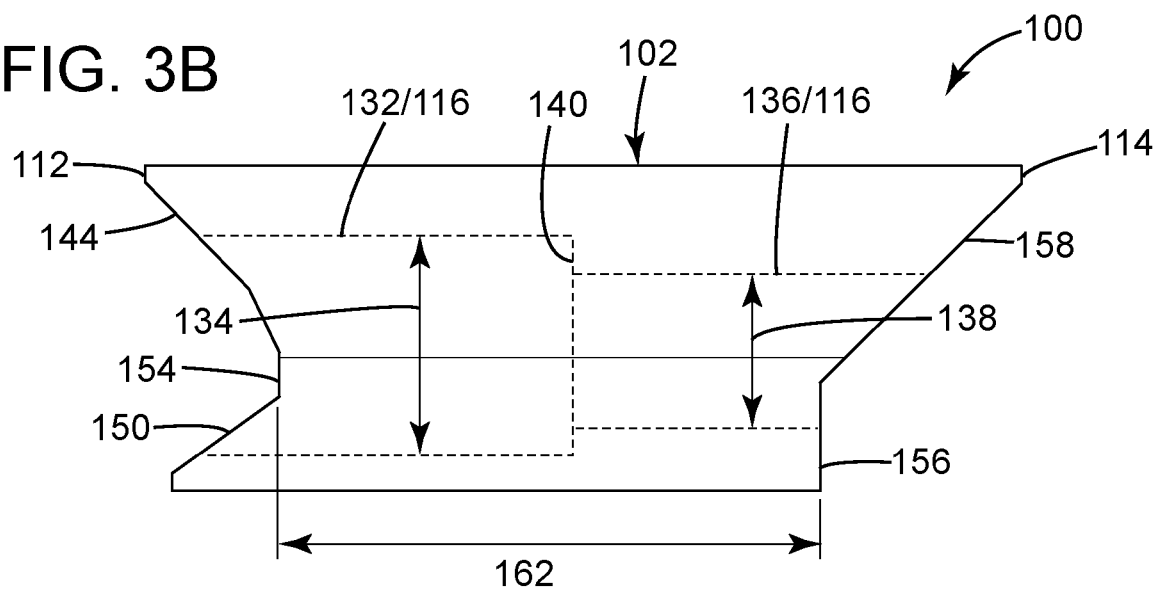
FIG. 3B depicts a side view of the spacer implant of FIG. 3A, according to aspects described herein.
Figure 3C:
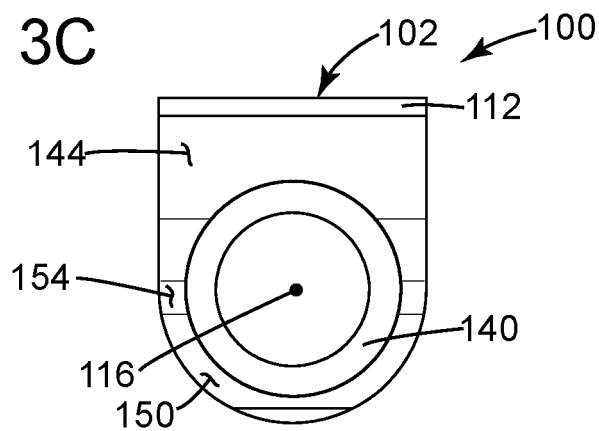
FIG. 3C depicts a front view of the spacer implant of FIG. 3A, according to aspects described herein.

The length 128 of the fastener portion 122 may vary based on a functional length 162 of the spacer insert 102 and a position of a hard stop 140 within the spacer implant 102 (see FIGS. 3A-C). The length 128 may be sized to ensure that a controlled depth of the fastener portion 122 (for example, only 5 to 7 mm of the fastener portion 122) enters into the lateral mass 118 before being stopped by the hard stop 140 within the spacer implant 102.

As will be discussed in greater detail herein, the head 120 of the fastener implant 104 may be designed in such a way that it would interfere with a change in diameter of the spacer implant tunnel 116, forming the aforementioned mechanical hard stop 140. The head 120 may also include a drive connection 130 disposed on a distal end of the head 120. The drive connection may be, for example, designed with a geometry that can be used with standard driver tool sizes, for example, tool sizes that are in conformance with ASTM F543—"Standard Specification and Test Methods for Metallic Medical Bone Screws".

Referring to FIGS. 3A, 3B and 3C, a perspective view (FIG. 3A), a side view (FIG. 3B) and a front view (FIG. 3C) of an embodiment of the spacer implant 102 of the laminoplasty implant system 100 is depicted, according to aspects described herein. In FIGS. 3A and 3B, the geometry of the tunnel 116 of the spacer implant 102 is shown in hidden dotted lines. In FIG. 3C, the geometry of the tunnel 116 can be seen directly.

The tunnel 116 of the spacer implant 102 may include a large diameter section 132 having a first diameter 134 and a small diameter section 136 having a second diameter 138, wherein the first diameter 134 is larger than the second diameter 138. The large and small diameter sections 132, 136 define a hard-stop 140 therebetween.

The head 120 of the fastener implant 104 may have a diameter 142 (see FIG. 2) sized to fit into the large diameter section 132 of the tunnel 116. A first portion of the head 120 may be configured to extend through the large diameter section 132 of the tunnel 116 and abut against the hard-stop 140, while a second portion of the head 120 may be configured to extend outwardly from the tunnel 116 and into the lamina 108 (see FIG. 1).

The first end 112 of the spacer implant 102 may include a superficial (or first) lamina flange 144 configured to extend over a superficial (or first) surface 146 of the lamina 108 to inhibit the spacer implant 102 from being pushed into a vertebral foramen 148 of the vertebra 110, when the spacer implant 102 is inserted into the interlaminal space 106 (see FIG. 1). The first end 112 of the spacer implant 102 may also include a deep (or second) laminal flange 150 configured to extend under a deep (or second) surface 152 of the lamina 108. The deep laminal flange 150 and the superficial laminal flange 144 secure the lamina 108, when the spacer implant 102 is inserted into the interlaminal space 106 (see FIG. 1). The first end 112 of the spacer implant 102 may also include a vertex surface 154 from which the superficial lamina flange 144 and the deep laminal flange 150 extend outwardly therefrom. The exact geometries of the first end 112 features may be optimized to accommodate and/or conform to different patient anatomies.

The second end 114 of the spacer implant 102 may include a lateral mass kick stand surface 156 configured to abut against the lateral mass 118 of the vertebra 110, when the spacer implant 102 is inserted into the interlaminal space 106. The second end 114 of the spacer implant 102 may also include a lateral mass flange 158 configured to extend over a superficial (or first) surface 160 of the lateral mass 118, when the spacer implant 102 is inserted into the interlaminal space 106.

A shortest distance between the lateral mass kick stand surface 156 and the vertex surface 154 defines a functional length 162 of the spacer implant 102. The functional length 162 determines the size of the interlaminal space 106. Spacer implants of different functional lengths 162 may be manufactured to accommodate best surgical practices and surgeon preferences.

An advantageous feature of the laminoplasty implant system 100 is the tunnel 116 of the spacer implant 102, which is a through hole that runs axially through the entire functional length 162 of the spacer implant 102. The tunnel 116, unlike previous laminoplasty implant systems, enables the fastener implant 104 to pass through the spacer implant 102, in such a way that both the elevated lamina 108 and the lateral mass 118 of the vertebra 110 are in contact with a single fastener implant 104. The embodiment of the tunnel 116 illustrated in FIGS. 3A-3C is shown as a counterbored hole with two diameters, the large diameter 134 of the large diameter section 132 and the small diameter 138 of the small diameter section 136. The large diameter section 132 may be dimensioned as a clearance hole sized for the head 120 of the fastener implant 104, while the small diameter section 136 may be dimensioned as a clearance hole sized for the threaded section 124 of the fastener implant 104. The change in diameter within the tunnel (where the large diameter section 132 and small diameter section 136 meet) creates the physical hard-stop 140, which prevents the fastener implant 104 from plunging too deep into the lateral mass 118 of the vertebra 110 (i.e., controls the depth of the fastener implant 104 into the lateral mass 118). Another advantageous feature of the laminoplasty implant system 100, is the functional length 162 of the spacer implant 102. The functional length 162 is the distance between the lateral mass kickstand surface 156 (which provides a physical contact with the lateral mass 118) and the vertex surface 154 where the superficial laminal flange 144 and the deep laminal flange 150 meet (which provides a physical contact with the lamina 108). The functional length 162 determines the size of the interlaminal space 106, which is dimensioned to provide a sufficient opening of the vertebral foramen 148 (e.g., 8 mm, 10 mm, 12 mm, 14 mm, 16 mm, 18 mm all of which are common sizes used by surgeons). The superficial laminal flange 144 and deep laminal flange 150 are designed to cradle the contacting surface of the lamina 108 (see FIG. 1). The deep laminal flange 150 provides a "shelf" under the deep surface 152 of the lamina 108 for the lamina 108 to rest on. The superficial laminal flange 144 extends over/into the superficial side of the lamina 108 to prevent the spacer implant 102 from being easily pushed down into the vertebral foramen 148. The lateral mass flange 158 similarly rests on the superficial surface 160 of the vertebra's lateral mass 118, preventing the lateral mass end (second end) 114 of the spacer implant 102 from plunging into the vertebral foramen 148.

Figure 4A:
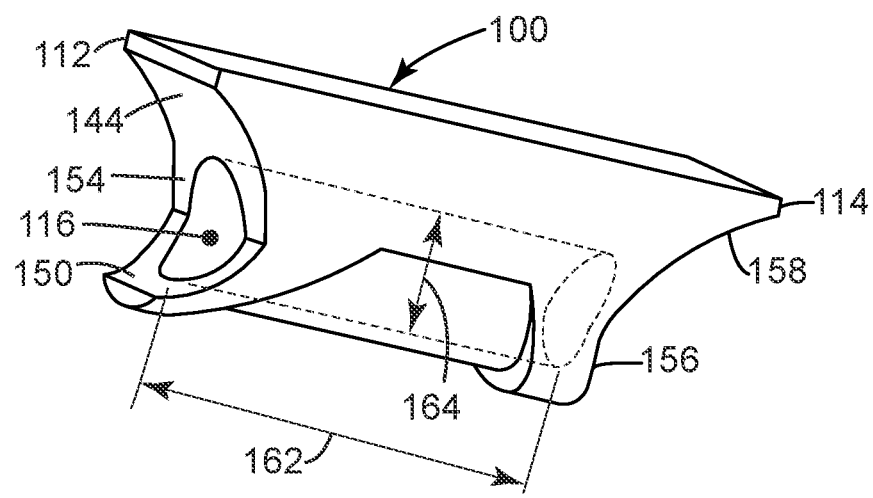
FIG. 4A depicts a perspective view of another embodiment of a spacer implant, wherein the tunnel has a single constant diameter therethrough, according to aspects described herein.

Referring to FIGS. 4A, a perspective view of another embodiment of the spacer implant 102 is depicted, wherein the tunnel 116 of the spacer implant 102 includes a single constant diameter 164 therethrough. In this case, the head 120 of the fastener implant 104 is configured to abut against the first end 112 of the spacer implant 102 as a hard stop. Additionally, the fastener portion 122 of the fastener implant 104 is configured to extend through the entire tunnel 116 and into the lateral mass 118 of the vertebra 110. The tunnel 116 may therefore be dimensioned as a constant diameter hole for just the threaded section 124 of the fastener portion 122 of the fastener implant 104. In this embodiment, the vertex surface 154 of the first end 112 of the spacer implant 102 may provide the hard stop for the head 120 of the fastener implant 104.

Figure 4B:
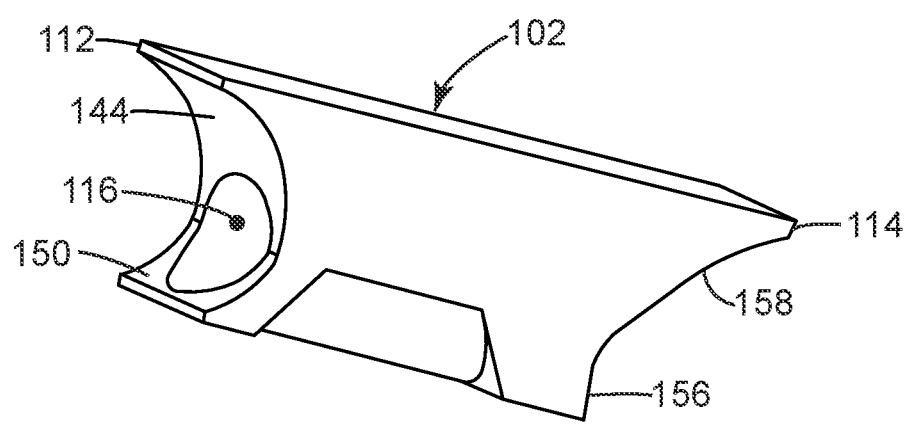
FIG. 4B depicts a perspective view of another embodiment of a spacer implant, according to aspects described herein.
Figure 4C:
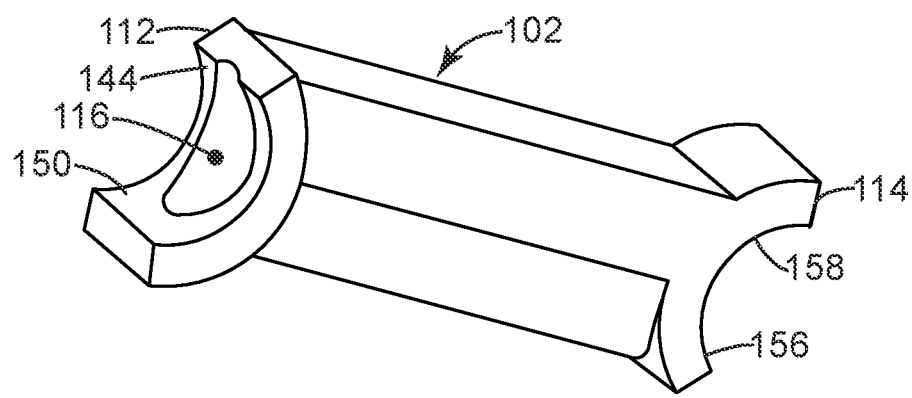
FIG. 4C depicts a perspective view of another embodiment of a spacer implant, according to aspects described herein.

Referring to FIGS. 4B and 4C, perspective views of other embodiments of the spacer implant 102 are depicted, according to aspects described herein. The spacer implant 102 in FIGS. 3A-3C and FIG. 4A is optimally configured for a C4 cervical vertebra. However, the spacer implant 102 may be optimized for other vertebrae in the spine as well. Accordingly, the dimensions and shapes of such features as, the functional length 162, the superficial laminal flange 144, the deep laminal flange 150, the lateral mass kickstand surface 156 and the lateral mass flange 158 would be altered for different vertebrae and differing patient anatomy. FIGS. 4B and 4C depict two other possible designs/geometries for the spacer implant 102.

Figure 5:
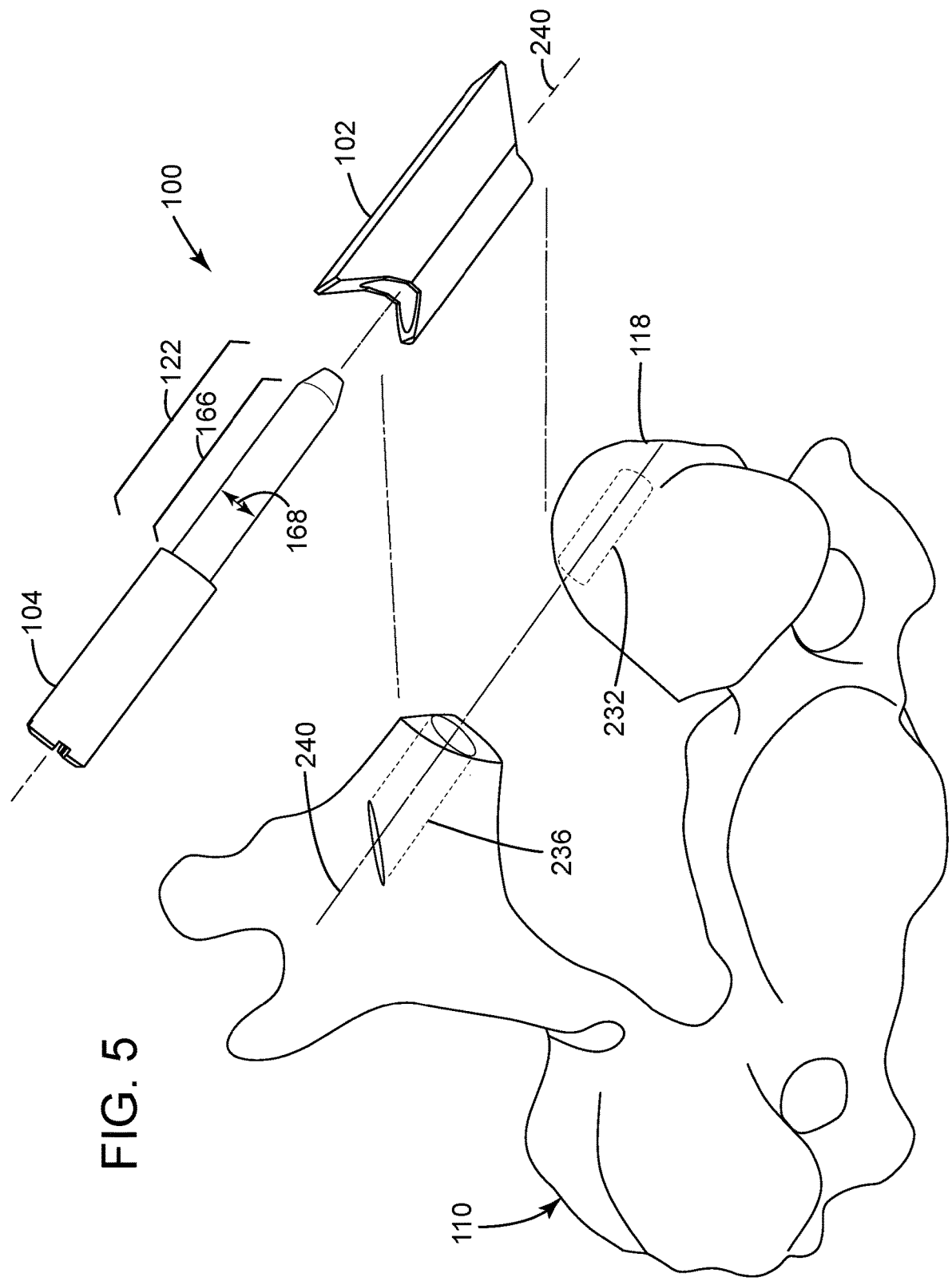
FIG. 5 depicts a perspective view of another embodiment of the fastener implant, wherein the fastener portion includes a pin section, according to aspects described herein.

Referring to FIG. 5, a perspective view of another embodiment of the fastener implant 104 is depicted, wherein the fastener portion 122 includes a pin section 166, according to aspects described herein. The pin section 166 may be configured to be press fit into a first pilot hole 232 bored into the lateral mass 118 of the vertebra 110. The pin section 166 would have a constant diameter 168 with no threaded section. The first pilot hole 232 may be sized to receive the pin section 166 and frictionally lock the pin section 166 in place within the lateral mass 118.

Figure 6:
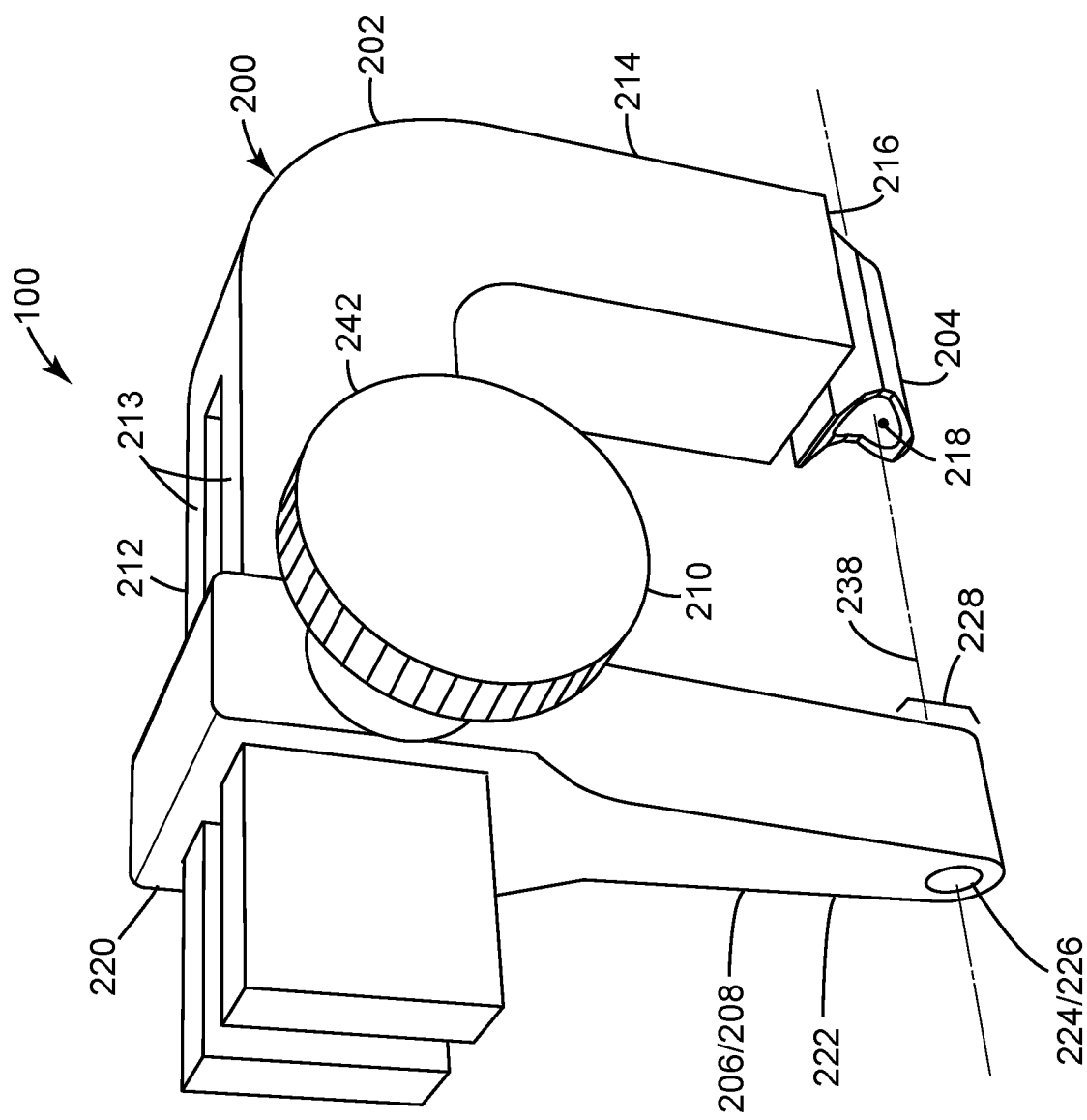
FIG. 6 depicts a perspective view of a drill guide of the laminoplasty spacer implant system of FIG. 1, according to aspects described herein.
Figure 7:
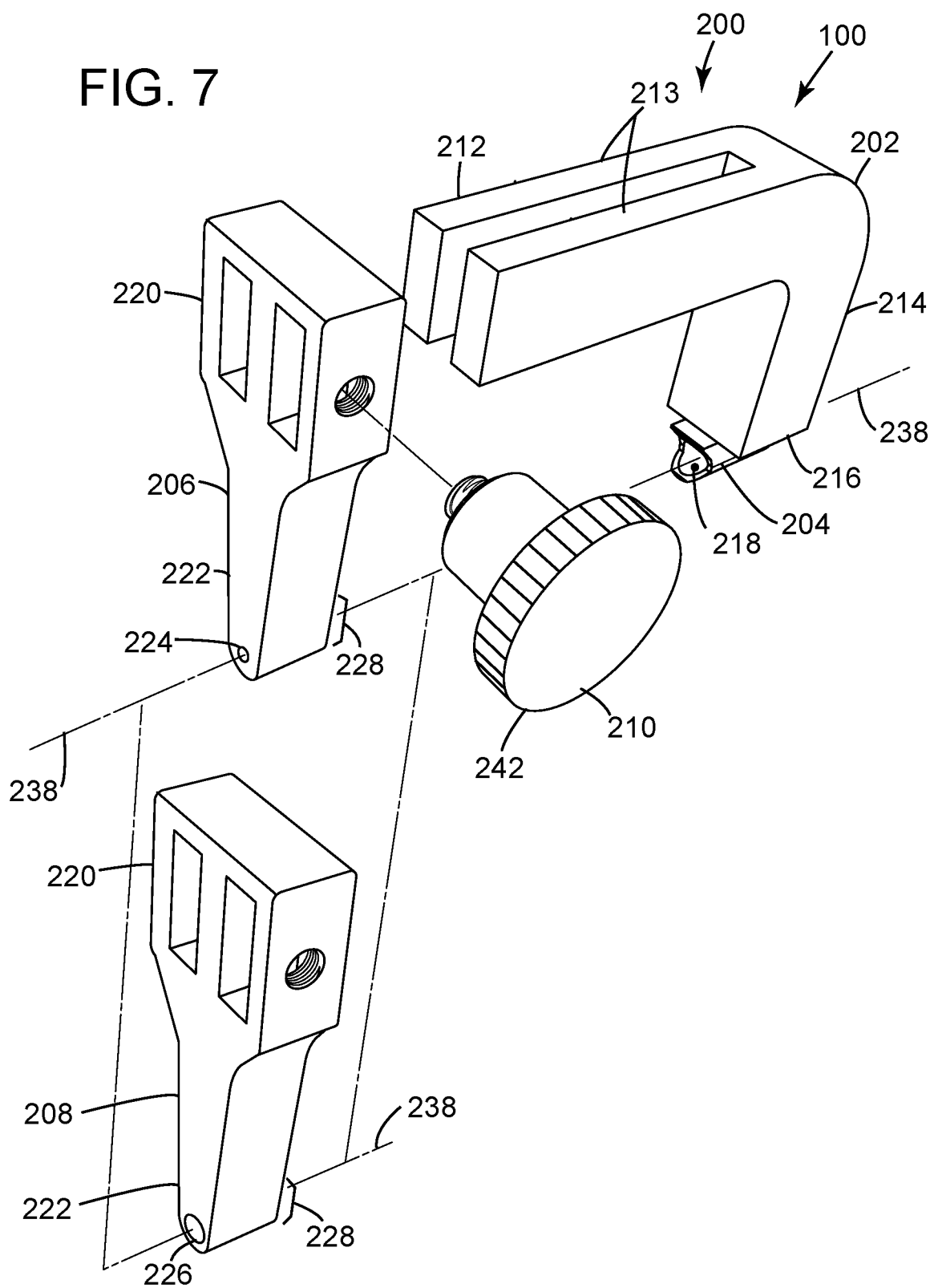
FIG. 7 depicts an exploded view of the drill guide of FIG. 6, according to aspects described herein.

Referring to FIGS. 6 and 7, a perspective view (FIG. 6) and an exploded view (FIG. 7) of a drill guide 200 of the laminoplasty spacer implant system 100, according to the aspects described herein. The drill guide 200 may include a drill guide handle (or handle) 202, a spacer implant mimic 204 positioned on the handle 202 or alternatively an actual spacer implant 102 detachably positioned on the handle 202 (see FIGS. 9A and 9B), one or more drill guide slider mates 206, 208 and a locking mechanism 210. The drill guide 200 may be made from medical grade materials, such as (but not limited to) Ti6A14V per ASTM standard F136, stainless steel or from radiolucent PEEK plastic, or the like material.

Advantageously, the drill guide 200 enables the user to utilize unique implant systems and methods to implant a spacer implant 102 with a single fastener implant 104 into an interlaminal space 106 of a vertebra 110 (see FIG. 1). The drill guide 200 enables these unique systems and methods by ensuring that for one or more pilot holes 232, 236 (see FIGS. 1 and 2) can be drilled at a correct angle through the cut elevated lamina 108 and the lateral mass 118 on opposing sides of the interlaminal space 106, such that the pilot holes 232, 236 are aligned and concentric with the tunnel 116 of the spacer implant 102. Accordingly, the single fastener implant 104 can then be accurately inserted through the pilot holes 232, 236 and the spacer implant 102 to fixate the spacer implant into the interlaminar space 106.

More specifically, the drill guide 200 may include a drill guide handle 202 having a first leg 212 and a second leg 214 positioned at substantially right angles relative to each other. A spacer implant mimic 204 may be positioned on a distal end 216 of the second leg 214. The spacer implant mimic 204 may have substantially the same geometric shape as the spacer implant 102 including a tunnel 218 of the spacer implant mimic 204 with the same geometric shape as the tunnel 116 of the spacer implant 102. Alternatively, as will be described in greater detail herein, an actual spacer implant 102 may be detachably positioned on the distal end 216 of the second leg 214 of the handle 202 (see FIGS. 9A and 9B).

The drill guide 200 may also include one or more drill guide slider mates 206, 208. The one or more drill guide slider mates 206, 208 include a mating section 220 configured to be slid over and positioned on the first leg 212. More specifically, the first leg 212 of the drill guide handle 202 may include two pronged portions 213 extending parallel to each other, wherein the mating section 220 of the one or more drill guide slider mates 206, 208 is configured to slide over the two pronged portions 213 of the first leg 212. The one or more drill guide slider mates 206, 208 also includes an extension section 222 extending away from the mating section 220. One or more drill guide holes 224, 226 are disposed in a distal end portion 228 of the extension section 222.

More specifically, the one or more drill guide slider mates 206, 208 may include a first drill guide slider mate 206 and a second drill guide slider mate 208. The first drill guide slider mate 206 includes a first drill guide hole 224 that is configured to guide a first drill bit 230 (see FIG. 11) in drilling a first pilot hole 232 into the lateral mass 118 of the vertebra 110. The first pilot hole 232 is sized to receive the fastener portion 122 of the fastener implant 104. The second drill guide slider mate 208 includes a second drill guide hole 226 that is configured to guide a second drill bit 234 (see FIG. 12) in drilling a second pilot hole 236 into the lamina 108 of the vertebra 110. The second pilot hole 236 being sized to receive the head 120 of the fastener implant 104. For example, the first drill guide slider hole 224 may be a 2 mm diameter guide hole to accommodate a 1.6 mm diameter first drill bit 230 (pilot hole drill bit for fastener portion 122 of fastener implant 104), and the second drill guide hole 226 may be a 4.4 mm diameter guide hole to accommodate a 4.0 mm diameter second drill bit 234 (counterbore drill bit for head 120 of fastener implant 104). The drill bits 230 and 234 may also have an additional stepped feature (not shown) on their heads that may abut against the drill guide slider mates 206, 208 or some other feature of the drill guide 200 to provide a hard stop to control the drill depth.

The drill guide 200 may also include a locking mechanism 210 configured to releasably lock the one or more drill guide slider mates 206, 208 into position on the first leg 212 of the drill guide handle 202. Advantageously, when the locking mechanism 210 locks the drill guide slider mates 206, 208 into position on the first leg 212, the drill guide hole 224, 226 has substantially the same center line 238, and is concentric with, the tunnel 116, 218 of the respective one of the spacer implant 102 or the spacer implant mimic 204 (see FIGS. 11 and 12) In other words, when the drill guide slider mates 206, 208 are locked into position on the first leg 212, the drill guide hole 224, 226 has the same center line 238, and is concentric with, the tunnel 116 of the spacer implant 102 or the tunnel 218 of the spacer implant mimic 204. The locking mechanism 210 can also prevent unwanted motion of the drill guide slider mates 206, 208.

Advantageously, the alignment of the first and second drill guide holes 224, 226 with either the tunnel 218 of the spacer implant mimic 204 or the tunnel 116 of the spacer implant 102, enables the first and second pilot holes 232, 236 to be drilled so that their centerlines 240 are also aligned with, and substantially the same as, the centerline of the tunnel 116 of the spacer implant 102, once the spacer implant 102 is inserted into the interlaminal space 106 (see FIGS. 1 and 2). Accordingly, the aforementioned alignments enable the single fastener implant 104 to be inserted through the first and second pilot holes 232, 236 and through the tunnel 116 to affix and secure the spacer implant 102 within the interlaminar space 106.

The locking mechanism 210, as illustrated in FIGS. 6 and 7, includes a thumb screw 242 that is threaded into the mating section 220 of the first and second drill guide slider mates 206, 208. The thumb screw 242 is easy to turn by hand, and presses against the first leg 212 of the drill guide handle 202 to lock the first and second drill guide slider mates 206, 208 into position. However, the locking mechanism 210 may include other types of locking devices, other than a thumb screw. For example, the locking mechanism 210 may include a spring-loaded locking mechanism or a pin locking mechanism.

Figure 8:
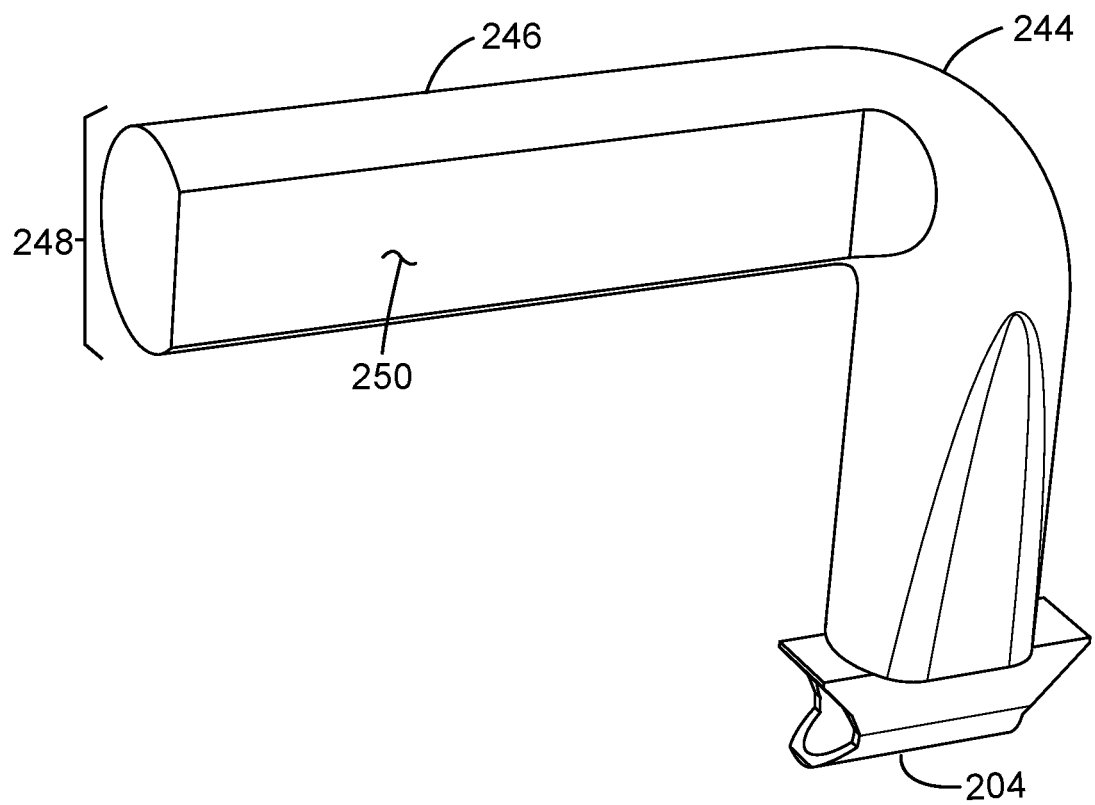
FIG. 8 depicts a perspective view of an embodiment of the handle of the drill guide of the laminoplasty implant system of FIG. 1, according to aspects described herein.

Referring to FIG. 8, a perspective view of another embodiment of the drill guide handle 244 of the drill guide 200 of the laminoplasty implant system 100 is depicted, according to aspects described herein. The drill guide handle 244 includes a first leg 246, which includes a single solid rod 248 having a flat surface 250 extending along a length of the first leg 246. The one or more drill guide slider mates 206, 208 are configured to slide over the single solid rod 248.

FIG. 6 illustrates the first leg 212 as including two pronged portions 213 and FIG. 8 illustrates the first leg 246 as including a single solid rod 248. However, other geometries and features of the first leg 212, 248 are also possible as long as those geometries and features of the first leg control orientation and accommodate locking of the drill guide slider mates 206, 208.

Figure 9A:
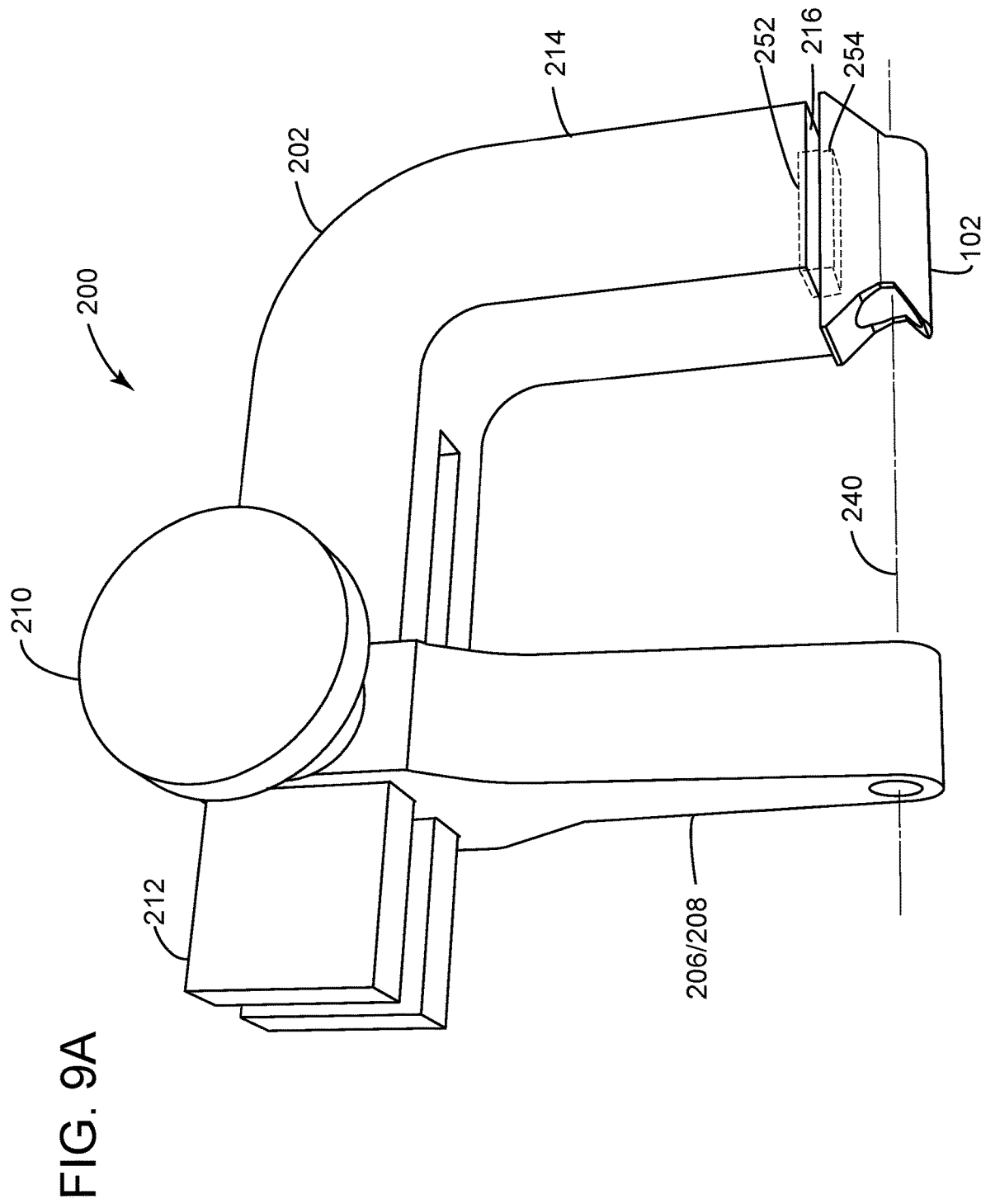
FIG. 9A depicts a perspective view of the drill guide of the laminoplasty implant system, wherein a spacer implant is removably attached to a distal end of a second leg of the handle, according to aspects described herein.
Figure 9B:
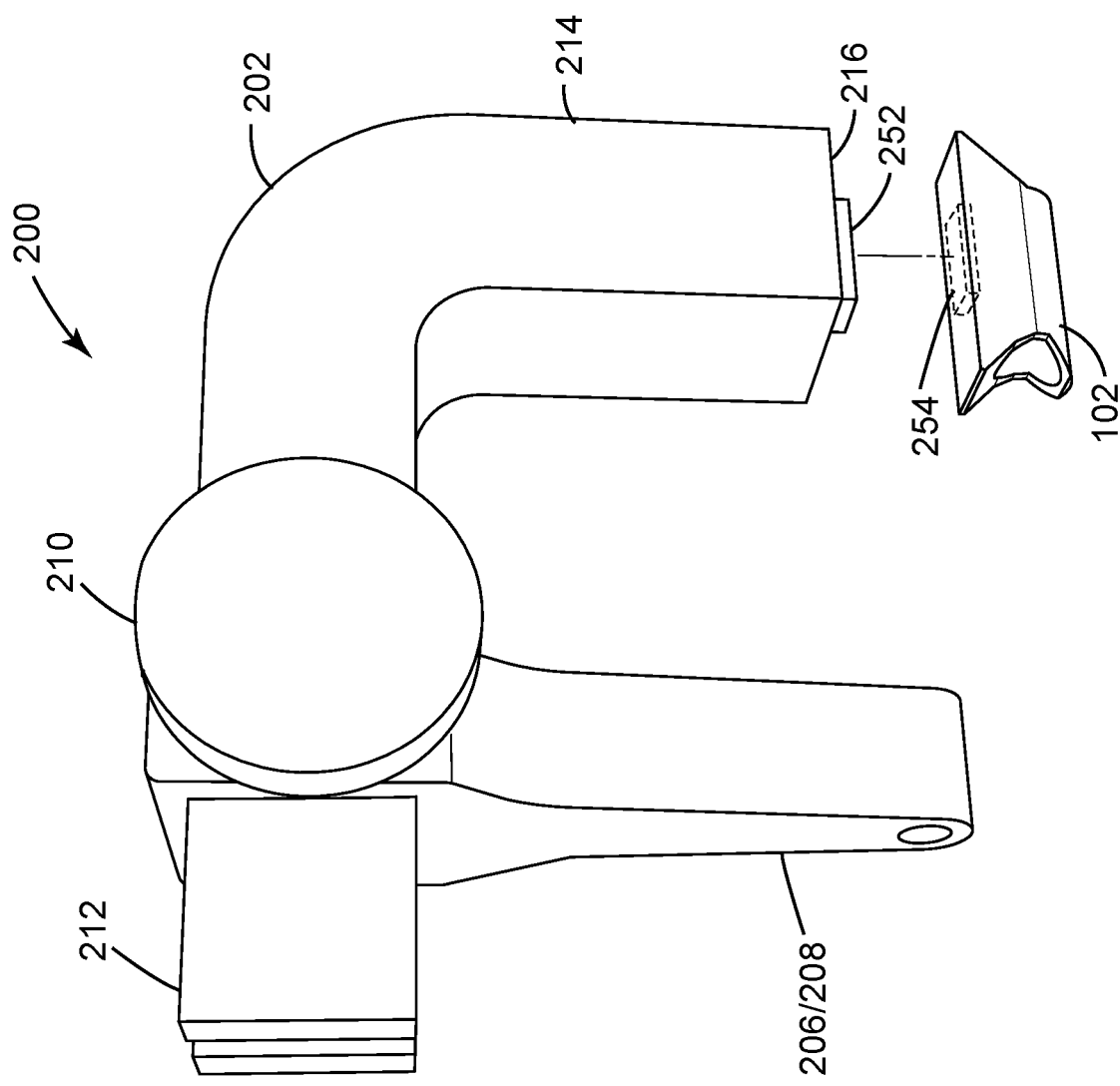
FIG. 9B depicts a perspective view of the drill guide of FIG. 9A, wherein the spacer implant is detached from the handle, according to aspects described herein.

Referring to FIGS. 9A and 9B, a perspective view of the embodiment of the handle 202 of the drill guide 200 of the laminoplasty implant system 100, wherein the spacer implant 102 is removably attached to the distal end 216 of the second leg 214 of the handle 202 (FIG. 9A), and wherein the spacer implant 102 is detached from the second leg 214 of the handle 202 (FIG. 9B), according to aspects described herein. In this embodiment, the spacer implant 102 is configured to be detachable from the distal end 216 of the second leg 214 of the drill guide handle 202, when the spacer implant 102 is inserted into the interlaminar space 106 and all the pilot holes 232, 236 have been drilled.

In this embodiment, the drill guide handle 202 may include a space implant locking mechanism 252 and the spacer implant 102 includes a handle locking mechanism 254. The spacer implant locking mechanism 252 and the handle locking mechanism 254 may be configured to lock together (see FIG. 9A) to temporarily attached the spacer implant 102 to the second leg 214 of the drill guide 200. The spacer implant 102 will be held in place on the drill guide 200 (in the lieu of the spacer implant mimic 204) while the pilot holes 232, 236 are drilled. The spacer implant 102 may then be detached from the drill guide 200 (see FIG. 9B). The fastener implant 104 may be inserted into the spacer implant 102, and fixated to the vertebra 110, before or after the spacer implant 102 is detached from the drill guide 200.

Figure 10:
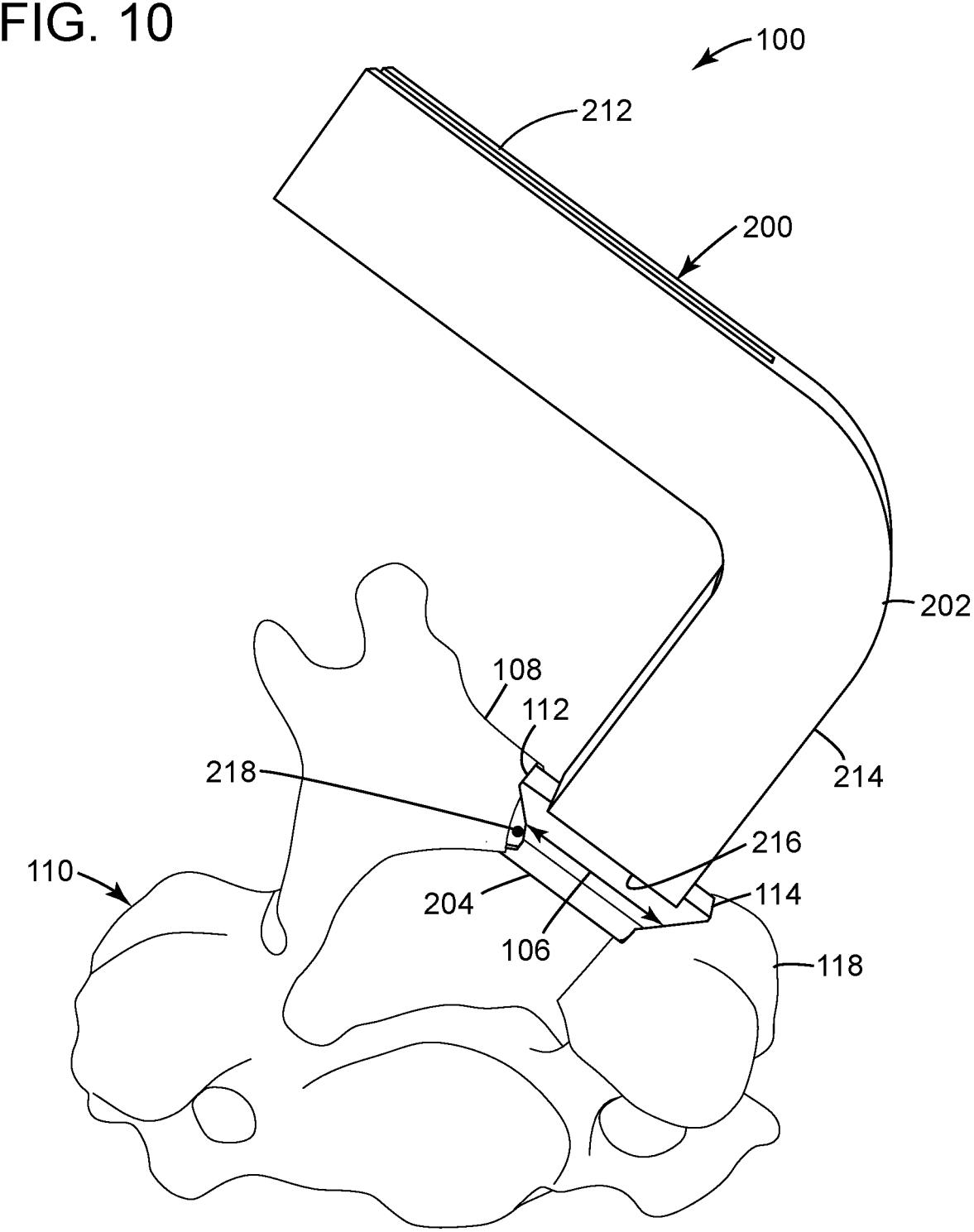
FIG. 10 depicts a spacer mimic, disposed on a second leg of the handle of the drill guide of the laminoplasty spacer implant system, being inserted into an interlaminal space of a vertebrae, according to aspects described herein.

Referring to FIG. 10, the first step of a method 300 of implanting a spacer implant 102 into an interlaminal space 106 of a vertebra 110 is depicted, according to the aspects described herein. The spacer implant mimic 204 is disposed on the distal end 216 of the second leg 214 of the handle 202 of the drill guide 200. The spacer implant mimic 204 has substantially the same geometric shape as a spacer implant 102 to be inserted, wherein both the spacer implant mimic 204 and the spacer implant 102 include a first end 112, a second end 114 and a tunnel 116 extending therebetween. The spacer implant mimic 204 is inserted into the interlaminal space 106 cut into the lamina 108 of the vertebra 110. The spacer implant mimic 204 holds open the interlaminal space 106 to a predetermined size and elevates the resected lamina 108.

Figure 11:
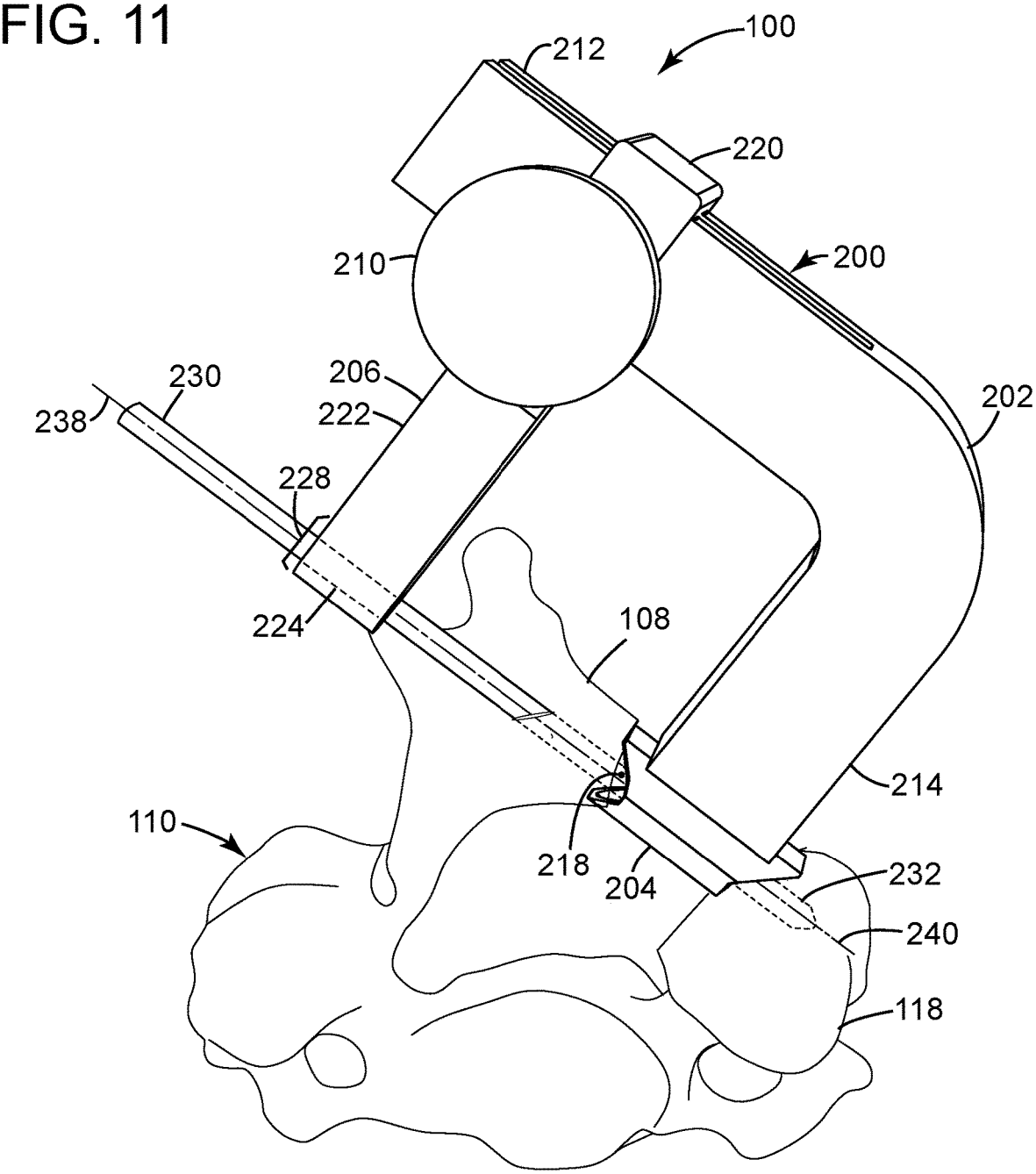
FIG. 11 depicts a first drill guide slider mate being positioned over a first leg of the handle and a first drill bit being used to drill a first pilot hole through the lamina and into a lateral mass side of the vertebral body, according to aspects described herein.

Referring to FIG. 11, second step of the method 300 is depicted, wherein the first drill guide slider mate 206 is positioned over the first leg 212 of the handle 202 of the drill guide 200 and the first drill bit 230 is used to drill the first pilot hole 232 in the lateral mass 118 of the vertebra 110, according to aspects described herein. The first drill guide slider mate 206 of the drill guide 200 is positioned over the first leg 212 of the handle 202 such that the first drill guide hole 224, that is disposed in the first drill guide slider mate 206, has substantially the same center line 238 as the tunnel 218 of the spacer implant mimic 204.

More specifically, the first drill guide slider mate 206 includes the mating section 220 that slides over the first leg 212 of the handle 202. The first drill guide slider mate 206 also includes an extension section 222 that extends away from the mating section 220. The first drill guide hole 224 is disposed in the distal end portion 228 of the extension section 222. The locking mechanism 210 locks the first drill guide slider mate 206 into place such that the centerline 238 of the first drill guide hole 224 and the tunnel 218 of the spacer implant mimic 204 is substantially the same.

Thereafter, the first drill guide hole 224 is utilized as a guide to drill the first pilot hole 232 into the lateral mass 118 of the vertebra 110. It is important to note that the centerline 240 of the first pilot hole 232 is also substantially the same as the centerline of the tunnel 218.

The first pilot hole 232 is drilled by the first drill bit 230. The first pilot hole 232 is drilled through the lamina 108, through the tunnel 218 of the spacer implant mimic 204, and then into the lateral mass 118 using the first (or small diameter) drill bit 230.

Figure 12:
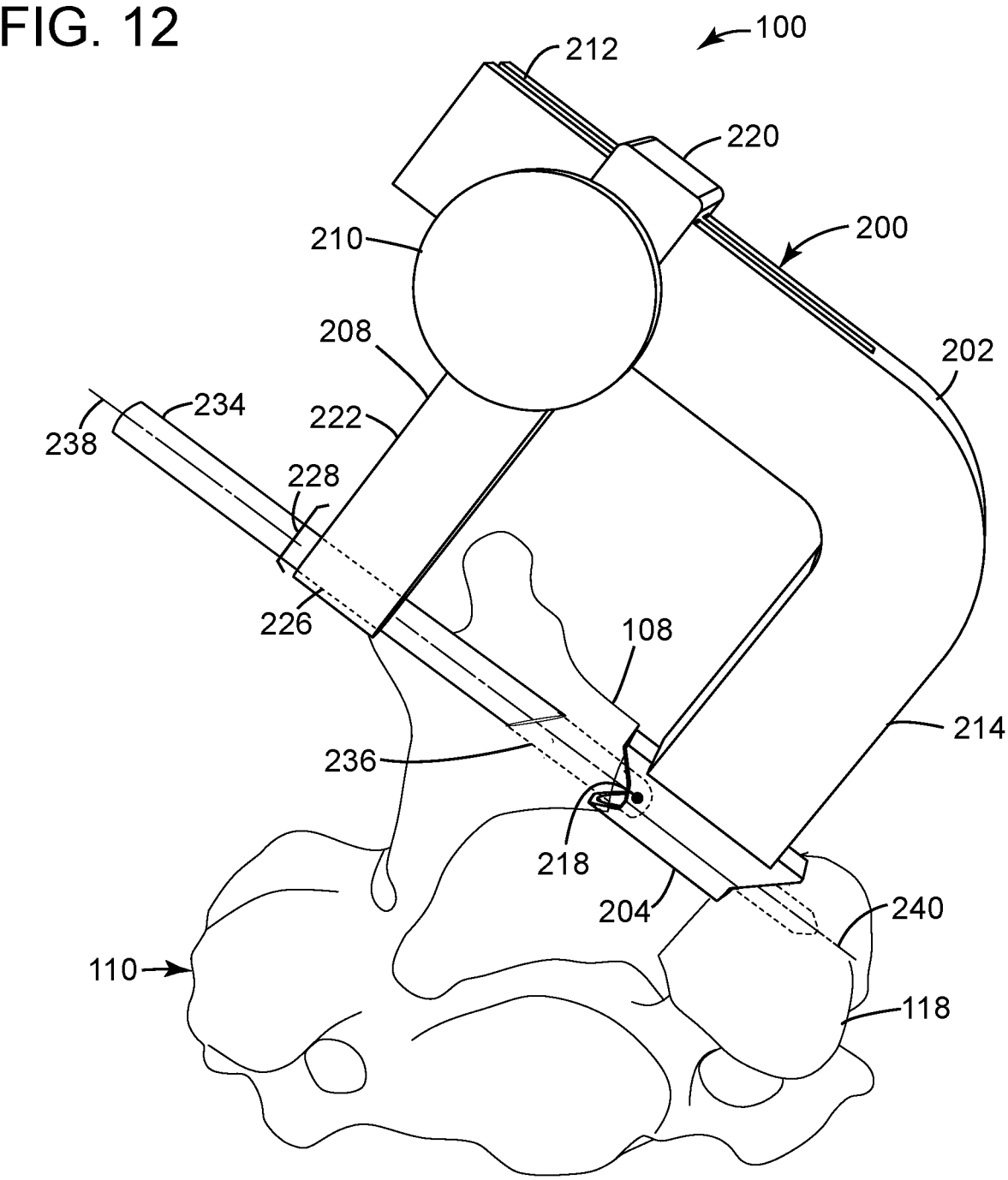
FIG. 12 depicts a continuation of the method of FIG. 10, wherein a second drill guide slider mate is positioned over the first leg of the handle and a second drill bit is used to drill a second pilot hole in a lamina of the vertebrae, according to aspects described herein.

Referring to FIG. 12, the next step of the method 300 is depicted, wherein the second drill guide slider mate 208 is positioned over the first leg 212 of the handle 202 and the second drill bit 234 is used to drill the second pilot hole 236 in the lamina 108 of the vertebra 110, according to aspects described herein. The second drill guide slider mate 208 of the drill guide 200 is positioned over the first leg 212 of the handle 202 such that the second drill guide hole 226, that is disposed in the second drill guide slider mate 208, has substantially the same center line 238 as the tunnel 218 of the spacer implant mimic 204.

More specifically, the second drill guide slider mate 208 includes the mating section 220 that slides over the first leg 212 of the handle 202. The second drill guide slider mate 208 also includes an extension section 222 that extends away from the mating section 220. The second drill guide hole 226 is disposed in the distal end portion 228 of the extension section 222. The locking mechanism 210 locks the second drill guide slider mate 208 into place such that the centerline 238 of the second drill guide hole 226 and the tunnel 218 of the spacer implant mimic 204 is substantially the same.

Thereafter, the second drill guide hole 226 is utilized as a guide to drill the second pilot hole 236 into the lamina 108 of the vertebra 110. It is important to note that the centerline 240 of the second pilot hole 236 is also substantially the same as the centerline of the tunnel 218.

The second drill bit 234 and the second drill guide hole 226 are larger than the first drill bit 230 and first drill guide hole 224, respectively. Accordingly, the second pilot hole 236 is a counterbore that is larger than the first pilot hole 232 and is sized to receive the head 120 of the fastener implant 104.

Figure 13:
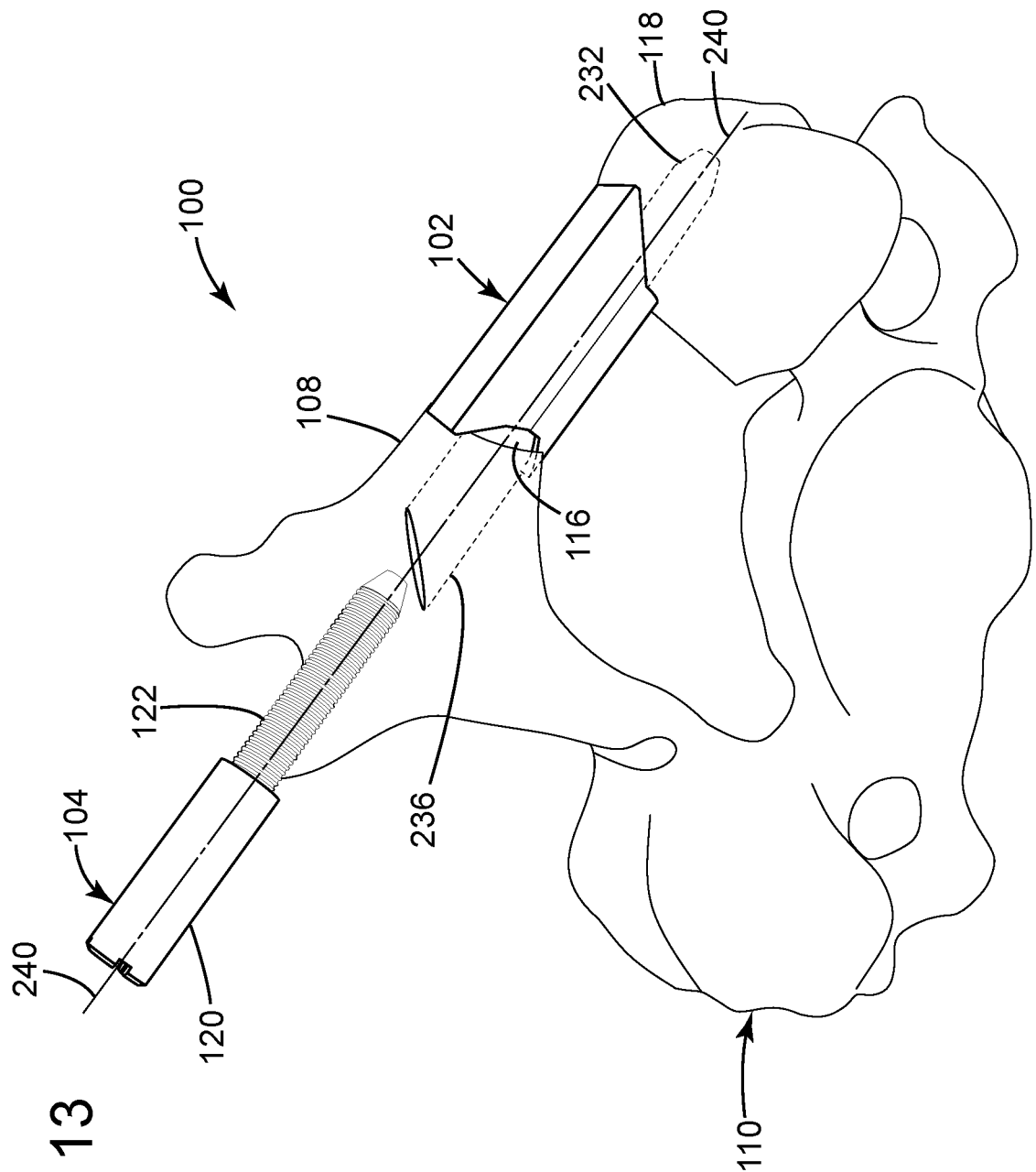
FIG. 13 depicts the handle being removed and a spacer implant being inserted into the interlaminal space in place of the spacer implant mimic, according to aspects described herein.

Referring to FIG. 13, the next step of the method 300 is depicted, wherein the handle 204 is removed and the spacer implant 102 is inserted into the interlaminal space 106 in place of the spacer implant mimic 204, according to aspects described herein. The drill guide 200 is removed from the vertebra 110 along with its spacer implant mimic 204 and the spacer implant 102 may be inserted in the interlaminal space 106 between the resected lamina 108 and the lateral mass 118. It is important to note that once the spacer implant 102 is inserted, the centerline 240 of the first and second pilot holes 232, 236 are substantially the same as the centerline 240 of the tunnel 116 of the spacer implant 102.

Figure 14:
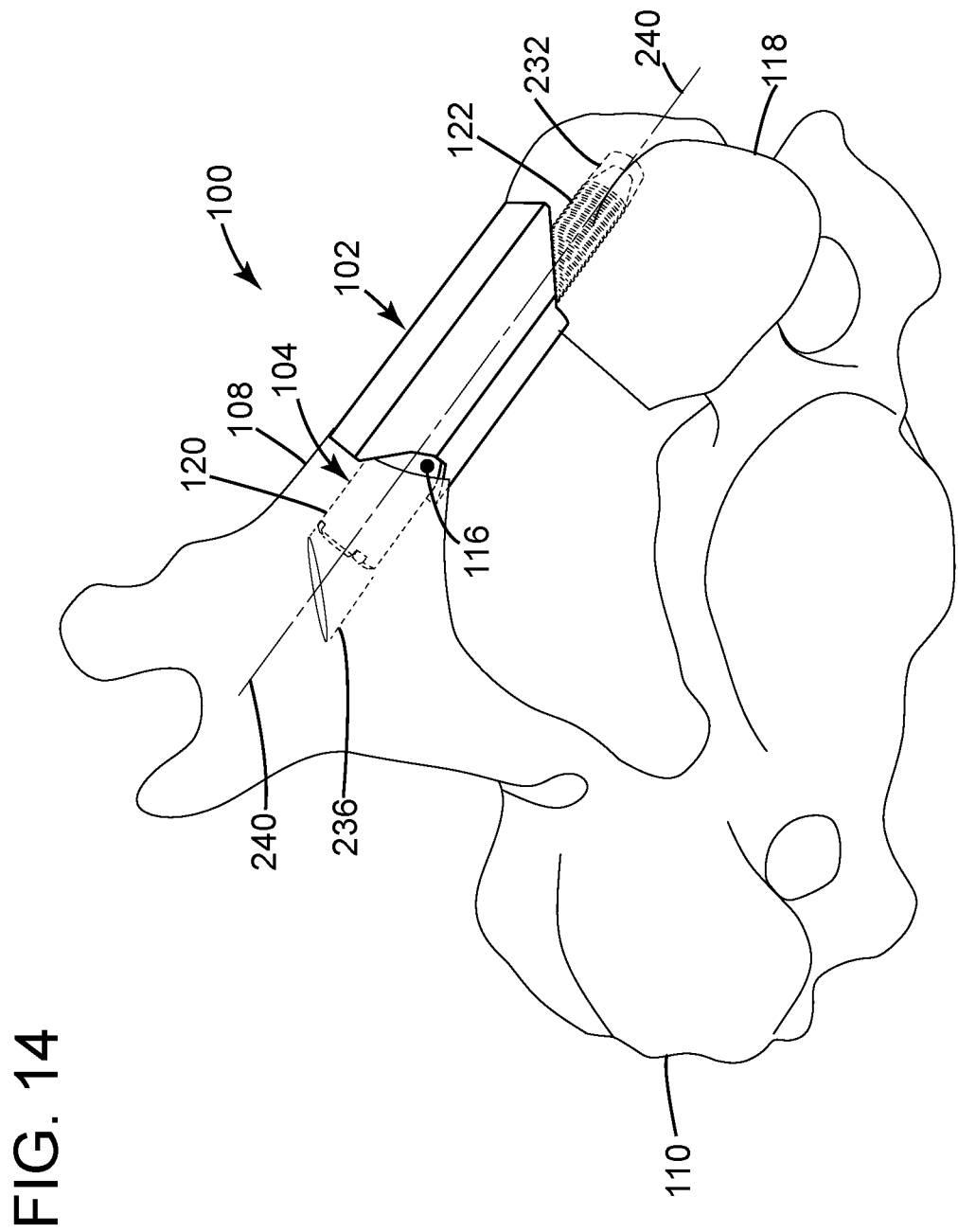
FIG. 14 depicts a fastener implant being implanted into the second pilot hole in the resected lamina, through the tunnel of the spacer implant, and into the first pilot hole in the lateral mass side of the vertebral body to secure the spacer implant and fastener implant in place within the interlaminal space, according to aspects described herein.

Referring to FIG. 14, subsequent step of the method 300 is depicted, wherein the fastener implant 104 is implanted into the second pilot hole 236 in the lamina 108, through the tunnel 116 of the spacer implant 102, and into the first pilot hole 232 in the lateral mass 118 to secure the spacer implant 102 and the fastener implant 104 in place within the interlaminal space 106, according to aspects described herein. The fastener implant 104 may be guided through the pre-drilled counterbore second pilot hole 236 in the lamina 108, through the spacer implant tunnel 116, and screwed into the lateral mass 118 to fixate the spacer implant 102 to the vertebra 110.

Advantageously, the centerline 240 is substantially the same for both the first and the second pilot holes 232, 236 and the spacer implant tunnel 116, so the single fastener implant 104 can easily and accurately be inserted into the spacer implant 102. Also advantageously, the head 120 of the fastener implant 104 abuts against the hard stop 140 formed between the large diameter section 132 and small diameter section 136 of the tunnel 116 (see FIGS. 3A-3C) to prevent the fastener portion 122 of the fastener implant 104 from penetrating too deep into the lateral mass 118 of the vertebra 110.

Figure 15:
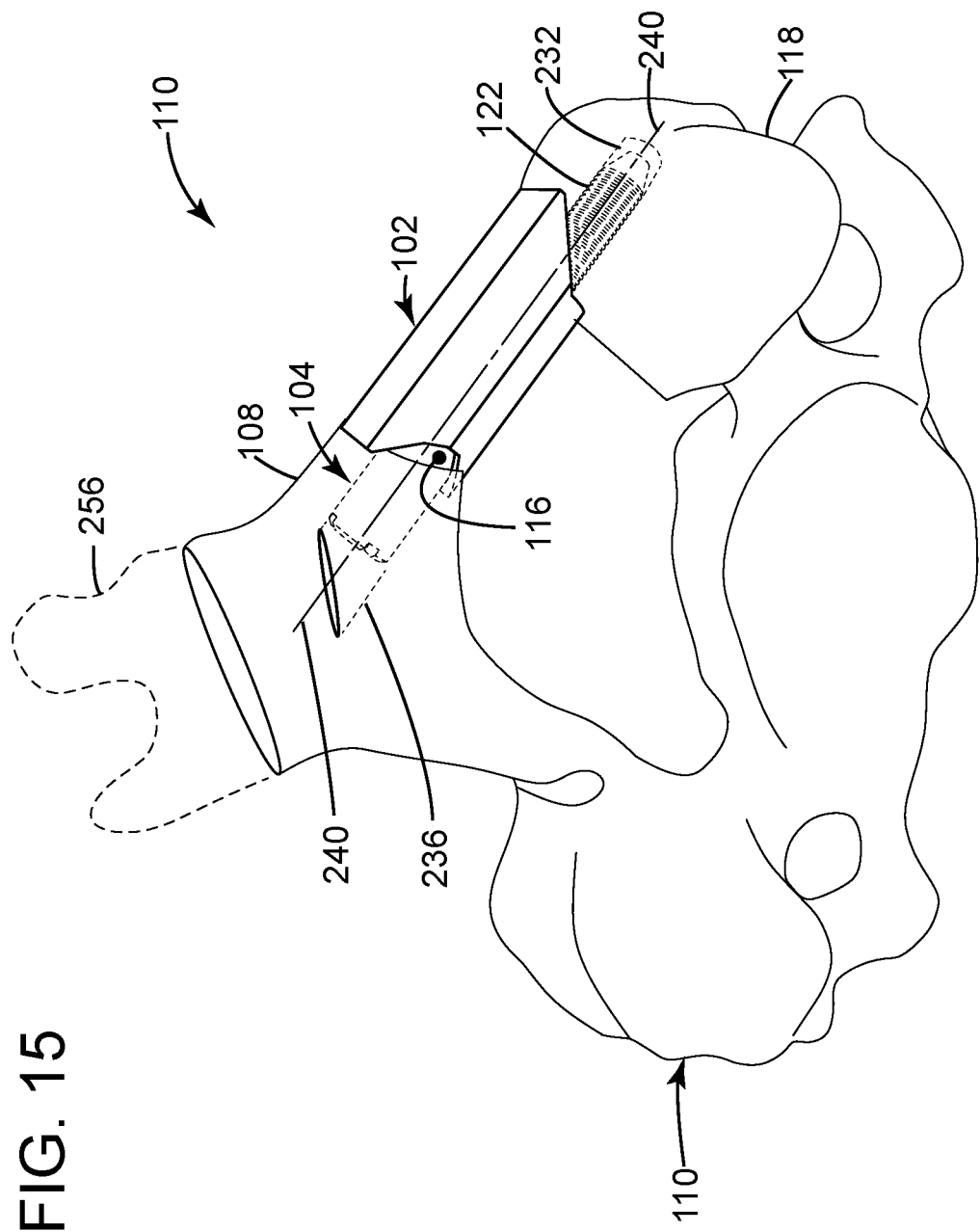
FIG. 15 depicts the resection of the spinous process from the vertebral body, according to aspects described herein.

Referring to FIG. 15, another step of the method 300 is depicted, wherein the vertebra 110 has its spinous process 256 removed (see ghosted dotted lines), according to aspects described herein. By removing the spinous process 256 when cutting the lamina 108 to form the interlaminal space 106, there is less, and a potentially more advantageous (i.e. flat), bone structure to drill through when drilling the first and second pilot holes 232, 236. The removal of the spinous process 256 may occur before any pilot holes are drilled or any of the implant system 100 is in place.

Figure 16:
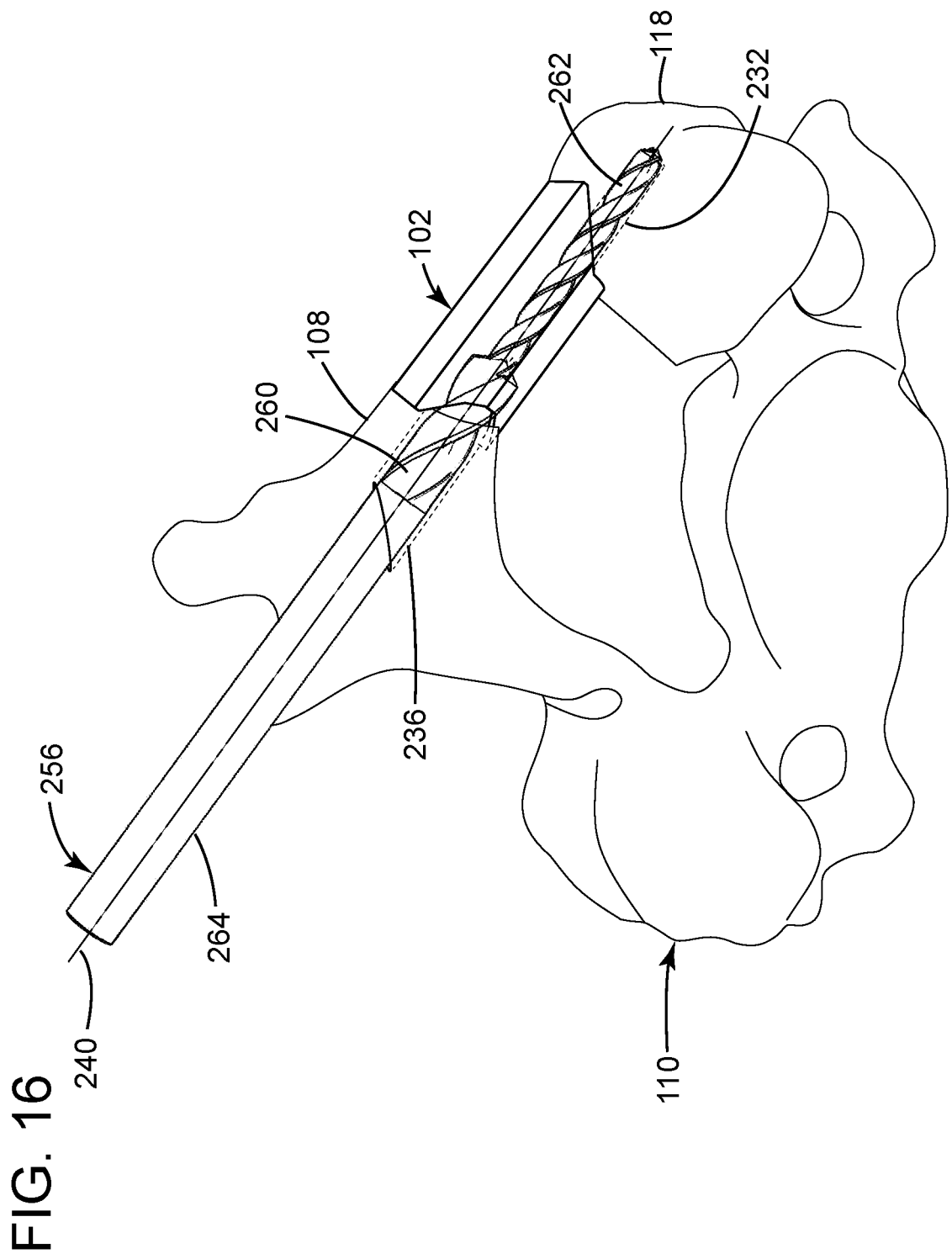
FIG. 16 depicts a drill bit having two different diameter cutting blades being utilized to drill two pilot holes simultaneously, according to aspects described herein.

Referring to FIG. 16, a modification of the method 300 is depicted, wherein the drill bit 258, having two different diameter cutting blades 260, 262, is utilized to cut the first and second pilot holes 232, 236 simultaneously, according to aspects described herein. Rather than two separate drill bits 230, 234 being used, a single stepped drill bit 258 as shown in FIG. 16, may be used to drill the pilot holes 232, 236. The method 300 would remain the same, except that only one drill guide slider mate would be required, therefore shortening the method 300. The length of the smaller diameter blades 260 would be dependent on the desired drill depth into the lateral mass 118 and the spacer implant functional length 162. The drill bit 258 may also have an additional stepped feature (not shown) on its head 264 that may abut against the drill guide slider mate 206 or some other feature of the drill guide 200 to provide a hard stop to control the drill depth.

The method 300 as shown uses a handle 202 with a spacer implant mimic 204 disposed on its second leg 214. However, substantially the same method 300 could be performed using a handle 202 with the actual spacer implant 102 removably attached to it second leg 214. The only difference would be that when the handle 202 is removed, the spacer implant 102 would be detached from the handle 202 and would remain in the interlaminal space 106.

Referring to FIG. 17, a flow diagram of the method 300 of implanting the spacer implant 102 into the interlaminal space 106 of the vertebra 110 as illustrated in FIGS. 10-15 is depicted, according to aspects described herein.

The method 300 begins at 302 by inserting the spacer implant mimic 204 disposed on the second leg 214 of the handle 202 of the drill guide 200 into the interlaminal space cut 106 into the lamina 108 of the vertebra 110 (see FIG. 10). The spacer implant mimic 204 has substantially the same geometric shape as the spacer implant 102, which is ultimately inserted and fixated into the interlaminal space 106. Both the spacer implant mimic 204 and the spacer implant 102 include the first end 112, the second end 114 and the tunnel 116, 218 extending therebetween.

At 304, the first drill guide slider mate 206 of the drill guide 200 is positioned over the first leg 212 of the handle 202 such that the first drill guide hole 224, that is disposed in the first drill guide slider mate 206 has substantially the same center line 238 as the tunnel 218 of the spacer implant mimic 204. More specifically, the mating section 220 of the first drill guide slider mate 206 is slid over the first leg 212 until the first drill guide slider mate 206 abuts against the vertebra 110. The locking mechanism 210 of the drill guide 200 is utilized to lock the first drill guide slider mate 206 into position. An extension section 222 of the first drill guide slider mate 206 is integrally connected to the mating section 220 and extends away from the mating section perpendicularly to the second leg 214 of the handle 202. The first drill guide hole 224 is disposed in the distal end portion 228 of the extension section 222 such that, when the first drill guide slider mate 206 is locked into position, the centerline 238 of the first drill guide hole 224 passes through the center of the tunnel 218 of the spacer implant mimic 204.

At 306, the first drill guide hole 224 is utilized as the guide to drill the first pilot hole 232 into the lateral mass 118 of the vertebra 110 (see FIG. 11). More specifically, the first drill bit 230 is slid through the first drill guide hole 224 and used to drill first through the lamina 108 on the lamina side of the spacer implant mimic 204 (i.e., the side of the spacer implant mimic 204 where the lamina 108 abuts against the first end 112 of the spacer implant mimic 204). The first drill bit 230 passes through the tunnel 218 of the spacer implant mimic 204 and drills the first pilot hole 232 into the lateral mass 118 on the lateral mass side of the spacer implant mimic 204 (i.e., the side of the spacer implant mimic 204 where the lateral mass 118 abuts against the second end 114 of the spacer implant mimic 204). The first pilot hole 232 is sized to receive the fastener portion 122 of the fastener implant 104.

At 308, a second drill guide slider mate 208 of the drill guide 200 is positioned over the first leg 212 of the handle 202 such that the second drill guide hole 226, that is disposed in the second drill guide slider mate 208 has substantially the same center line 238 as the tunnel 218 of the spacer implant mimic 204.

At 310, the second drill guide hole 226 is utilized as the guide to drill the second pilot hole 236 into the cut or resected lamina 108 of the vertebra 110 (see FIG. 12). More specifically, the second drill bit 234 is slid through the second drill guide hole 226 and used to drill through the cut lamina 108 on the lamina side of the spacer implant mimic 204. The second pilot hole 236 is larger than the first pilot hole 232 and is sized to receive the head 120 of the fastener implant 104.

At 312, the spacer implant 102 is inserted into the interlaminal space 106 in place of the spacer implant mimic 204 (see FIG. 13). The spacer implant 102 may be inserted using forceps or other like surgical tools. Advantageously, because of the alignment of the first and second drill guide holes 224, 226, the centerline 240 of the first and second pilot holes 232, 236, passes through the center of the tunnel 116 of the spacer implant 102.

At 314, a fastener implant 104 is implanted through the second pilot hole 236 in the cut/resected lamina 108, the tunnel 116 of the spacer implant 102 and the first pilot hole 232 in the lateral mass 118 to secure the spacer implant 102 and fastener implant 104 in place within the interlaminal space 106.

At 316, the spinous process 256 of the vertebra 110 is removed prior to cutting the first or second pilot holes 232, 236. By removing the spinous process 256 when cutting the lamina 108 to form the interlaminal space 106, there is less, and a potentially more advantageous (i.e. flat), bone structure to drill through when drilling the first and second pilot holes 232, 236.

Referring to FIG. 18, a flow diagram of an alternative method 400 of implanting the spacer implant 102 into the interlaminal space 106 of a vertebra 110 is depicted, according to aspects described herein.

The method 400 begins at 402, by inserting one of the spacer implant 102 or the spacer implant mimic 204 disposed on the second leg 214 of the handle 202 of the drill guide 200, into an interlaminal space 106 cut into the lamina 108 of the vertebra 110. The spacer implant mimic 204 has substantially the same geometric shape as the spacer implant 102, wherein both the spacer implant mimic 204 and the spacer implant 102 include a first end 112, a second end 114 and a tunnel 116, 218 extending therebetween. In the case of the spacer implant mimic 204, the spacer implant mimic 204 may be permanently attached to the distal end 216 of the second leg 214 (see FIG. 6). In the case of the spacer implant 102, both the spacer implant 102 and the second leg 214 may have complementary locking mechanisms 252, 254 that enable the spacer implant 102 to be removably attached to the distal end 216 of the second leg 214 (see FIGS. 9A and 9B).

At 404, one or more drill guide slider mates 206, 208 of the drill guide 200 are positioned over the first leg 212 of the handle 202 such that one or more drill guide holes 224, 226, that are disposed in the one or more drill guide slider mates 206, 208, have substantially the same center line 238 as the tunnel 116, 218 of the respective one of the spacer implant 102 or the spacer implant mimic 204.

In the case of positioning only one drill guide slider mate, if a drill bit 258, having two different diameter cutting blades 260, 262 (see FIG. 16), is utilized to cut the first and second pilot holes 232, 236 simultaneously, then only one drill guide slider mate may be utilized rather than two. The drill guide slider mate would be the second drill guide slider mate 208, which has the larger second drill guide hole 226 sized for the head 120 of the fastener implant 104.

In the case of positioning more than one drill guide slider mates, the first and second drill guide slider mates 206, 208 may be used. Accordingly the first and second drill bits 230, 234 would be used to drill the first and second pilot holes 232, 236 in separate steps.

At 406, the one or more drill guide holes 224, 226 are utilized as one or more guides to drill the first pilot hole 232 into the lateral mass 118 of the vertebra 110 and the second pilot hole 236 into the cut lamina 108 of the vertebra 110. This may be done with a single larger second drill guide hole 226 using, for example, the two blade drill bit illustrated in FIG. 16, or both the first and second drill guide holes 224, 226 using, for example, the first and second drill bits 230, 234.

At 408, the spacer implant 102 is detached from the drill guide 200, if the spacer implant 102 is attached to the second leg 214 of the drill guide 200. More specifically, if the actual spacer implant 102 is removably attached to the distal end 216 of the second leg 214 by, for example, locking mechanisms 252, 254 as illustrated in FIGS. 9A and 9B, then the spacer implant 102 must be detached from the drill guide handle 202 prior to removing the handle 202 from the interlaminal space 106. Since the spacer implant 102 is already inserted into the interlaminal space 106, and may be additionally fixed with the fastener implant 104, it will remain there as the handle 202 is removed. It should be noted, that detaching 408 of the spacer implant 102 from the drill guide 200 may occur before or after implanting 412 of the fastener implant 102 as described below.

At 410, the spacer implant is inserted into the interlaminal space 106 in place of the spacer implant mimic 204, if the spacer implant mimic 204 is attached to the second leg 214 of the drill guide 202. More specifically, if the spacer implant mimic 204 is permanently attached to the distal end 216 of the second leg 214 (see FIG. 6), then the spacer implant mimic 204 must be removed from the interlaminal space when the drill guide 200 is removed, and the actual spacer implant 102 must be inserted in place of the spacer implant mimic 204.

At 412, the fastener implant 104 is implanted through the second pilot hole 236 in the lamina 108, the tunnel 116 of the spacer implant 102 and the first pilot hole 232 in the lateral mass 118 to secure the spacer implant 102 and the fastener implant 104 in place within the interlaminal space 106.

Advantageously, because of the alignment of the centerline 238 of the first and second drill guide holes 224, 226 with the tunnel 116, 218 of either the spacer implant 102 or spacer implant mimic 218, the centerline 240 of the first and second pilot holes 232, 236, passes through the center of the tunnel 116 of the spacer implant 102 when the spacer implant 102 is inserted into the interlaminal space 106. Accordingly, the single fastener implant 104 can be accurately and easily implanted through the second pilot hole 236 in the lamina 108, through the tunnel 116 of the spacer implant 102 and through the first pilot hole 232 in the lateral mass 118 to secure the spacer implant 102 and the fastener implant 104 in the interlaminal space 106.

The fastener implant 104 may be threaded into the first pilot hole 232 in the lateral mass 118 until the head 120 of the fastener implant 104 abuts against a portion of the spacer implant 102 as a hard stop to advantageously prevent the fastener portion 122 of the fastener implant 104 from penetrating too far into the lateral mass 118. The hard stop 140 may be formed at the intersection of the large diameter section 132 and the small diameter section 136 within the tunnel 116 of the spacer implant 102 (see FIGS. 3A-3C). The hard stop 140 may also be the first end 112 of the spacer implant 102 if the tunnel 116 of the spacer implant 102 is a constant diameter sized for just the fastener portion 122 of the fastener implant 104 (see FIG. 4A).

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. A laminoplasty implant system, comprising:
a spacer implant configured for insertion into an interlaminal space defined by a cut into a lamina of a vertebra, the spacer implant comprising:
a first end and a second end, and
a tunnel extending axially between the first end and the second end; and
a single fastener implant configured for insertion through the tunnel when the spacer implant is inserted into the interlaminal space, the fastener implant comprising:
a head configured to abut against a portion of the spacer implant and to extend axially from the first end into the lamina of the vertebra, and
a fastener portion configured to extend through the tunnel and to extend axially from the second end into a lateral mass of the vertebra.

2. The implant system of claim 1, comprising:
the tunnel of the spacer implant comprising a large diameter section having a first diameter and a small diameter section having a second diameter, wherein the first diameter is larger than the second diameter, and wherein the large and small diameter sections define a hard-stop therebetween; and
the head of the fastener implant has a diameter sized to fit into the large diameter section of the tunnel, wherein the head is configured to extend through the large diameter section of the tunnel and abut against the hard-stop.

3. The implant system of claim 1, comprising:
the tunnel of the spacer implant comprising a single constant diameter therethrough;
the head of the fastener implant being configured to abut against the first end of the spacer implant; and
the fastener portion of the fastener implant being configured to extend through the entire tunnel and into the lateral mass of the vertebra.

4. The implant system of claim 1, wherein the fastener portion of the fastener implant comprises a threaded section configured to be threaded into a hole bored into the lateral mass of the vertebra.

5. The implant system of claim 1, wherein the fastener portion of the fastener implant comprises a pin portion configured to be press fit into a hole bored into the lateral mass of the vertebra.

6. The implant system of claim 1, wherein the first end of the spacer implant comprises:
   a first lamina flange configured to extend over a first surface of the lamina to inhibit the spacer implant from being pushed into a vertebral foramen of the vertebra, when the spacer implant is inserted into the interlaminal space;
   a second laminal flange configured to extend under a second surface of the lamina, such that the second laminal flange and the first laminal flange secure the lamina, when the spacer implant is inserted into the interlaminal space; and
   a vertex surface from which the first lamina flange and the second laminal flange extend outwardly therefrom.

7. The implant system of claim 6, wherein the second end of the spacer implant comprises:
   a lateral mass kick stand surface configured to abut against the lateral mass of the vertebra, when the spacer implant is inserted into the interlaminal space; and
   a lateral mass flange configured to extend over a first surface of the lateral mass, when the spacer implant is inserted into the interlaminal space.

8. The implant system of claim 7, wherein a shortest distance between the lateral mass kick stand surface and the vertex surface defines a functional length of the spacer implant, wherein the functional length determines the size of the interlaminal space.

9. The implant system of claim 1, wherein the vertebra is at least one of a cervical vertebrae, a thoracic vertebrae or a lumbar vertebrae.

10. The implant system of claim 1, further comprising a drill guide, the drill guide comprising:
   a drill guide handle having a first leg and a second leg positioned at substantially right angles relative to each other;
   one of the spacer implant or a spacer implant mimic being positioned on a distal end of the second leg;
   one or more drill guide slider mates comprising:
      a mating section configured to be slid over and positioned on the first leg,
      an extension section extending away from the mating section, and
      a drill guide hole disposed in a distal end portion of the extension section; and
   a locking mechanism configured to releasably lock the one or more drill guide slider mates into position on the first leg of the drill guide handle;
   wherein, when the locking mechanism locks the one or more drill guide slider mates into position on the first leg, the centerline of the drill guide hole is concentric with a tunnel of the respective one of the spacer implant or the spacer implant mimic.

11. The implant system of claim 10, wherein the one or more drill guide slider mates comprise:
   a first drill guide slider mate comprising a first drill guide hole configured to guide a first drill bit in drilling a first pilot hole into the lateral mass of the vertebra, the first pilot hole being sized to receive the fastener portion of the fastener implant; and
   a second drill guide slider mate comprising a second drill guide hole configured to guide a second drill bit in drilling a second pilot hole into the lamina of the vertebra, the second pilot hole being sized to receive the head of the fastener implant.

12. The implant system of claim 10, wherein:
   the one of the spacer implant or the spacer implant mimic is the spacer implant; and
   the spacer implant is detachable from the distal end of the second leg of the drill guide handle, when the spacer implant is inserted into the interlaminal space.

13. The implant system of claim 10, wherein the spacer implant mimic has substantially the same geometric shape as the spacer implant.

14. The implant system of claim 10, wherein:
   the first leg of the drill guide handle comprises two pronged portions, and
   the mating section of the drill guide slider mate is configured to slide over the two pronged portions.

15. The implant system of claim 10, wherein:
   the first leg of the drill guide handle comprises a rod having a flat surface extending along a length of the first leg, and
   the one or more drill guide slider mates are configured to slide over the rod.

16. A method of implanting a spacer implant into an interlaminal space of a vertebra, the method comprising:
   inserting one of a spacer implant or a spacer implant mimic disposed on a second leg of a handle of a drill guide, into the interlaminal space defined by a cut into a lamina of the vertebra, the spacer implant mimic having substantially the same geometric shape as the spacer implant, wherein both the spacer implant mimic and spacer implant include a first end, a second end and a tunnel extending therebetween;
   positioning one or more drill guide slider mates of the drill guide over a first leg of the handle such that one or more drill guide holes disposed in the one or more drill guide slider mates have substantially the same center line as the tunnel of the respective one of the spacer implant or spacer implant mimic;
   utilizing the one or more drill guide holes as one or more guides to drill a first pilot hole into a lateral mass of the vertebra and a second pilot hole into the lamina of the vertebra;
   detaching the spacer implant from the drill guide, if the spacer implant is attached to the second leg of the drill guide;
   inserting the spacer implant into the interlaminal space in place of the spacer implant mimic, if the spacer implant mimic is attached to the second leg of the drill guide; and
   implanting a fastener implant through the second pilot hole in the lamina, the tunnel of the spacer implant and the first pilot hole in the lateral mass to secure the spacer implant and fastener implant in place within the interlaminal space.

17. The method of claim 16, wherein the positioning and the utilizing further comprise:
   positioning a first drill guide slider mate of the one or more drill guide slider mates over the first leg of the handle, the first drill guide slider mate having a first drill guide hole of the one or more drill guide holes disposed therethrough;
   utilizing the first drill guide hole as a guide to drill the first pilot hole into the lateral mass of the vertebra;
   positioning a second drill guide slider mate of the one or more drill guide slider mates over the first leg of the handle, the second drill guide slider mate having a second drill guide hole of the one or more drill guide holes disposed therethrough; and utilizing the second drill guide hole as a guide to drill the second pilot hole into the lamina of the vertebra.

18. The method of claim 16, wherein the implanting further comprises:

screwing a threaded fastener portion of the fastener implant into the first pilot hole in the lateral mass until a head of the fastener implant abuts against a portion of the spacer implant.

19. The method of claim 18, wherein the head of the fastener implant abuts against a hard stop within the tunnel of the spacer implant.

20. The method of claim 16, wherein the utilizing further comprises:

utilizing the one or more drill guide holes as a guide to drill the first and second pilot holes with a single drill bit having two different diameter cutting blades.

* * * * *